United States Patent [19]

Yoshioka et al.

[11] Patent Number: 4,985,426

[45] Date of Patent: Jan. 15, 1991

[54] ARALKYLAMINOPYRIMIDINE DERIVATIVE, PROCESS FOR PRODUCING THEREOF AND INSECTICIDE, ACARICIDE AND FUNGICIDE CONTAINING SAID DERIVATIVE AS ACTIVE INGREDIENT

[75] Inventors: Hirosuke Yoshioka, Wako; Tokio Obata, Ube; Katsutoshi Fujii, Ube; Kiyoshi Tsutsumiuchi, Ube; Haruo Yoshiya, Ube, all of Japan

[73] Assignees: Ube Industries, Ltd., Ube; The Institute of Physical and Chemical Research, Wako, both of Japan

[21] Appl. No.: 435,937

[22] Filed: Nov. 13, 1989

Related U.S. Application Data

[62] Division of Ser. No. 105,403, Dec. 7, 1987, Pat. No. 4,895,849.

[30] Foreign Application Priority Data

Oct. 8, 1986 [JP] Japan ................. 61-237878
May 6, 1987 [JP] Japan ................. 62-108899
Sep. 10, 1987 [JP] Japan ................. 62-225180

[51] Int. Cl.$^5$ ................. A01N 43/54; C07D 239/42
[52] U.S. Cl. ................. 514/241; 514/252; 514/258; 514/259; 514/269; 544/215; 544/229; 544/238; 544/284; 544/296; 544/319; 544/326; 544/327; 544/328
[58] Field of Search ................. 544/215, 229, 238, 284, 544/296, 319, 326, 327, 328; 514/241, 252, 256, 258, 259, 269

[56] References Cited

U.S. PATENT DOCUMENTS 4,435,402 3/1984 Tsuji et al. ................. 544/326
4,617,393 10/1986 Bagli et al. ................. 544/319
4,627,872 12/1986 Schwamborn et al. ................. 544/319

Primary Examiner—Mary C. Lee
Assistant Examiner—Zinna Northington-Davis
Attorney, Agent, or Firm—Frishauf, Holtz, Goodman & Woodward

[57] ABSTRACT

There is disclosed a compound represented by the formula:

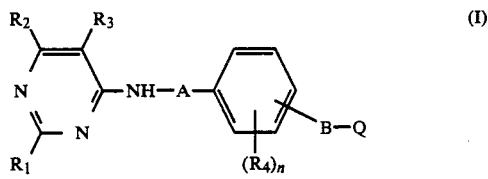

(I)

wherein $R_1$ represents a hydrogen atom or a lower alkyl group; $R_2$ and $R_3$ each independently represent a halogen atom or a lower alkyl group; $R_4$ represents a hydrogen atom, a halogen atom or a lower alkyl group; n represents an integer of 1 or 2; Q represents a phenyl group or a heterocyclic group; a substituted or unsubstituted alkyl group; an allyl group, a geranyl group; a farnesyl group; a cycloalkylmethyl group; a substituted ethyl group; a glycidyl group; an acetonyl group; a substituted dioxoranyl group; a 2,2-diethoxyethyl group, a 1-ethoxycarbonylethyl group, a trimethylsilylmethyl group or a 1-pyridylethyl group; A represents a lower alkylene group; and B represents a direct bond, an oxygen atom, a sulfur atom, a straight or branched lower alkylene group or a lower alkyleneoxy group;

or an acid addition salt thereof, a process for producing the same, and an insecticide, an acaricide and a fungicide containing the derivative as the active ingredient.

4 Claims, No Drawings

ARALKYLAMINOPYRIMIDINE DERIVATIVE, PROCESS FOR PRODUCING THEREOF AND INSECTICIDE, ACARICIDE AND FUNGICIDE CONTAINING SAID DERIVATIVE AS ACTIVE INGREDIENT

This is a division of application Ser. No. 07/105,403 filed Dec. 7, 1987 now U.S. Pat. No. 4,895,849.

BACKGROUND OF THE INVENTION

This invention relates to an aralkylaminopyrimidine derivative, a process for producing thereof and an insecticide, an acaricide and a fungicide containing said derivative as the active ingredient.

Some aralkylaminopyrimidine derivatives have been known in the art. For example, Journal of American Chemical Society (J.A.C.S), 80, p. 2189 (1958) discloses 4-benzylamino-6-chloropyrimidine and 4-furylamino-6-chloropyrimidine as diuretic intermediates, and no insecticidal or acaricidal activity can be recognized in these compounds. Also, Japanese Provisional Patent Publication No. 36666/1984 discloses an aminopyrimidine derivative represented by the following formula:

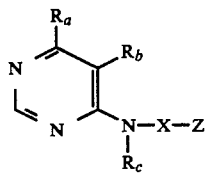

wherein $R_a$ and $R_b$ each represent a lower alkyl group or a halogen atom, or $R_a$ and $R_b$ are bonded to represent a trimethylene group or a tetramethylene group; $R_c$ represents a hydrogen atom or a lower alkyl group; X represents an alkylene group; Z represents a substituted or unsubstituted phenyl group (said substituent is one or two selected from a halogen atom, a lower alkyl group and a lower alkoxy group), a furyl group or a thienyl group.

The above known compound has fungicidal, insecticidal and acaricidal activities, and effective against important injurious insects in agriculture and horticulture such as diamondback moth, two-spotted spider mite, etc. and also against serious diseases in agriculture and horticulture such as powdery mildew, anthracnose, early blight, late blight, blast, etc.

However, these compounds are not sufficient in activity as the insecticidal and acaricidal agents.

The present inventors have intensively studies in order to obtain compounds having further excellent insecticidal, acaricidal and fungicidal activities than the above known compounds, and consequently found that by substituting the substituent when Z in the above formula is a phenyl group with specific substituents, insecticidal and acaricidal activities are remarkably improved, to accomplish the present invention.

SUMMARY OF THE INVENTION

This invention provides a compound represented by the formula (I):

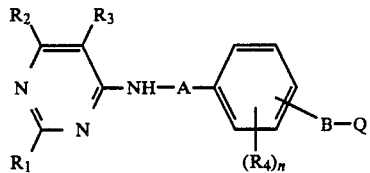

wherein $R_1$ represents a hydrogen atom or a lower alkyl group which is unsubstituted or substituted with a halogen atom; $R_2$ and $R_3$ each independently represent a halogen atom or a lower alkyl group which is unsubstituted or substituted with a halogen atom, a lower alkoxy group or a lower alkylthio group; $R_4$ represents a hydrogen atom, a halogen atom or a lower alkyl group; n represents an integer of 1 or 2; Q represents a phenyl group or a heterocyclic group each of which is unsubstituted or substituted with at least one selected from the group consisting of a halogen atom, a nitro group, a lower alkoxy group, a lower alkylthio group, a lower alkyl group which is unsubstituted or substituted with a halogen atom or a lower alkoxy group, a phenyl group which is unsubstituted or substituted with a lower alkoxy group and a phenoxy group which is unsubstituted or substituted with a halogen atom or an unsubstituted or halogen atom-substituted lower alkyl group; said heterocyclic group may be substituted with an oxo group; an alkyl group having 5 to 10 carbon atoms; an allyl group; a geranyl group; a farnesyl group; a lower alkyl group substituted with 1 to 4 halogen atoms; a cycloalkylmethyl group having 3 to 6 carbon atoms; an ethyl group substituted with a lower alkoxy group, a lower alkoxyalkyl group, a lower alkylthio group, a lower alkylsulfonyl group or a phenoxy group which may be substituted with one or two lower alkyl groups; a glycidyl group; an acetonyl group; a dioxoranyl group substituted with a phenoxymethyl group which may be substituted with a chlorine atom; a 2,2-diethoxyethyl group, a 1-ethoxycarbonylethyl group, a trimethylsilylmethyl group, a 1-pyridylethyl group, a lower alkyl group substituted with a benzylimino group which may be substituted with a lower alkoxyimino group or a lower alkyl group; A represents a lower alkylene group which is unsubstituted or substituted with one or two substituents selected from the group consisting of a cycloalkyl group having 3 to 5 carbon atoms, a lower alkynyl group, a lower alkyl group substituted with a halogen atom, a lower alkoxy group or a lower alkylthio group; and B represents a direct bond, an oxygen atom, a sulfur atom, a straight or branched lower alkylene group or a lower alkyleneoxy group;

or an acid addition salt thereof, a process for producing the same, and an insecticide, an acaricide and a fungicide containing said derivative as the active ingredient.

DESCRIPTION OF THE PREFERRED EMBODIMENT

In the above formula (I), the halogen atom may include a fluorine atom, a chlorine atom, a bromine atom and an iodine atom.

The lower alkyl group refers to a straight or branched alkyl group having 1 to 5 carbon atoms. Such alkyl groups may include a methyl group, an ethyl group, a propyl group, an isopropyl group, a butyl group, an isobutyl group, a sec-butyl group, a t-butyl group, an amyl group, an isoamyl group, a sec-amyl group, a sec-isoamyl group (a 1,2-dimethylpropyl group), a t-amyl group (a 1,1-dimethylpropyl group), etc.

The lower alkoxy group refers to a straight or branched alkoxy group having 1 to 5 carbon atoms. Such alkoxy groups may include a methoxy group, an ethoxy group, a propoxy group, an isopropoxy group, a butoxy group, an isobutoxy group, a sec-butoxy group, a t-butoxy group, an amyloxy group, etc.

The lower alkylthio group refers to a straight or branched alkylthio group having 1 to 5 carbon atoms. Such alkylthio groups may include a methylthio group, an ethylthio group, a propylthio group, an isopropylthio group, a butylthio group, an amylthio group, etc.

The cycloalkyl group having 3 to 5 carbon atoms may include a cyclopropyl group, a cyclobutyl group and a cyclopentyl group.

The lower alkynyl group refers to a straight or branched alkynyl group having 2 to 5 carbon atoms. Such alkynyl groups may include an ethynyl group, a propargyl group, a 1-propynyl group, etc.

The lower alkylene group refers to a group in which a chain member is a straight or branched alkylene group having 1 to 5 carbon atoms. Such alkylene groups may include a methylene group, an ethylene group, a trimethylene group, a tetramethylene group, a pentamethylene group, —CH(CH$_3$)—, —CH(C$_2$H$_5$)—, —CH(n—C$_3$H$_7$)—, —CH(i-C$_3$H$_7$)—, —CH(t-C$_4$H$_9$)—, —CH(n—C$_5$H$_{11}$)—, —,

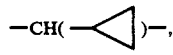

—C(CH$_3$)$_2$—, —C(CH$_3$) (C$_2$H$_5$)—, —CH(CH$_3$)—CH$_2$—, —CH(C$_2$H$_5$)—CH$_2$CH$_2$—, etc.

The lower alkyleneoxy group refers to a group in which a chain member is a straight or branched alkyleneoxy group having 1 to 5 carbon atoms. Such alkyleneoxy group may include —OCH$_2$—, —OCH(CH$_3$)—, —OCH$_2$CH$_2$—, —OCH$_2$CH$_2$CH$_2$—, etc. R$_1$ may preferably be a hydrogen atom and a methyl group.

When R$_2$ and/or R$_3$ are a lower alkyl group, they may preferably be a methyl group and an ethyl group. When the lower alkyl group is substituted with a halogen atom (a haloalkyl group), they may preferably be a fluoromethyl groups. When they are a halogen atom, they may preferably be a chlorine atom and a bromine atom. More preferably, R$_2$ is an ethyl group and R$_3$ is a chlorine atom, a bromine atom or a methyl group.

R$_4$ may preferably be a hydrogen atom.

n may preferably be an integer of 1.

In the above formula (I), Q represents a phenyl group or a heterocyclic group which is unsubstituted or substituted with specific substituent. Here, the heterocyclic group includes all heterocyclic groups containing 1 to 4 hetero atoms in the ring, and particularly, 5- or 6-membered monocyclic groups and fused heterocyclic groups containing these monocyclic groups are preferred. Such preferred heterocyclic groups may include 5-membered monocyclic groups such as a furyl group, a thienyl group, a pyrrolyl group, an oxazolyl group, an isooxazolyl group, a thiazolyl group, an isothiazolyl group, an imidazolyl group, a pyrazolyl group, an oxadiazolyl group and a tetrazolyl group; 6-membered monocyclic groups such as a pyranyl group, a pyridyl group, a pyridazinyl group, a pyrimidinyl group, a pyrazinyl group and a triazinyl group; and fused heterocyclic groups such as a benzothiazolyl group, a benzooxazolyl group, a benzoimidazolyl group, a thienopyrimidinyl group, a furopyrimidinyl group, an isooxazolopyrimidinyl group, a pyridopyrimidinyl group, a quinazolinyl group, a quinolyl group and a quinoxalinyl group.

When the above-mentioned phenyl group or heterocyclic group represented by Q is substituted, the number of substituents is not particularly limited, but may preferably be 1 to 3. Such substituents may preferably include a methyl group, an ethyl group, a t-butyl group, a trihalogenated methyl group, a methoxy group, a methylthio group, a fluorine atom, a chlorine atom and a nitro group.

When the Q is an alkyl group having 5 to 10 carbon atoms, an isoamyl group or a sec-amyl group is preferred, and it is a lower alkyl group substituted with 1 to 4 halogen atoms, a 2-fluoroethyl group, a 2,2,2-trifluoroethyl group, a 1,1,2,2-tetrafluoroethyl group or a 2,2-difluoropropyl group is preferred. Also, when the Q is an alkyl group substituted with a lower alkoxy group, a lower alkoxyalkyl group, a lower alkylthio group, a lower alkylsulfonyl group or a phenoxy group which may be substituted with one or two of lower alkyl groups, preferred are a 2-ethoxyethyl group, a 2-(2-ethoxyethoxy)ethyl group, a 2-ethylthioethyl group and a 2-ethoxysulfonylethyl group, and when it is a dioxoranylmethyl group substituted with a phenoxymethyl group which may be substituted with a halogen atom, preferred are a dioxorane-2-yl-methyl group and a 2-(4-chlorophenoxymethyl)dioxorane-4-yl-methyl group. Further, when the Q is a 1-pyridylethyl group, a 1-(pyridine-2-yl)ethyl group or a 1-(pyridine-4-yl)ethyl group is preferred and it is a lower alkyl group substituted with a benzylimino group which may be substituted with a lower alkoxyimino group or a lower alkyl group, a 2-methoxyiminoethyl group or a 2-methoxyiminopropyl group is preferred.

When A represents a lower alkylene group substituted with a lower alkyl group, it may preferably be a methylene group substituted with a methyl group, an ethyl group, an isopropyl group or an amyl group. When A represents a lower alkylene group substituted with a cycloalkyl group having 3 to 5 carbon atoms, it may preferably be a methylene group substituted with a cyclopropyl group.

B may preferably be an oxygen atom or a methylene group.

The group: —B—Q should be substituted preferably at the 3-position or 4-position relative to A.

Among the above-mentioned preferred compounds, more preferred is the compound represented by the formula (I'):

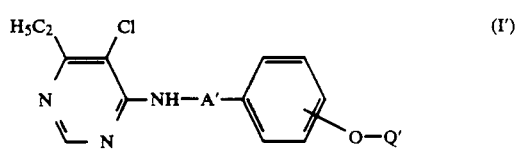

wherein A' represents a methylene group substituted with a methyl group, and an ethyl group, an isopropyl group or a cyclopropyl group; Q' represents a phenyl group which is substituted with a fluorine atom, a chlorine atom or a methyl group at the 4-position, or a 2-pyridyl group, a 5-chloropyridine-3-yl group, a 5-chloro-6-ethylpyrimidine-4-yl group, a 5-chloro-6-methylpyrimidine-4-yl group or a 6-chloro-5-methylpyrimidine-4-yl group; and the group: -O-Q' is substituted at the 3-position or 4-position relative to A'.

Another aspect of the present invention provides a more preferred compound represented by the following formula (I''):

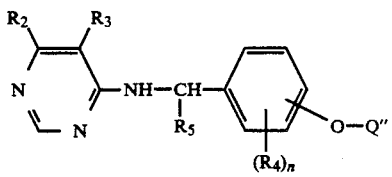

wherein $R_2$, $R_3$, $R_4$ and n have the same meanings as defined above; $R_5$ represents a lower alkyl group or a cycloalkyl group having 3 to 5 carbon atoms; and Q'' represents an alkyl group having 5 to 10 carbon atoms, an allyl group, a geranyl group, a farnesyl group, a lower alkyl group substituted with 1 to 4 halogen atoms, a cycloalkylmethyl group having 3 to 6 carbon atoms, a lower alkoxy group, a lower alkoxy alkyl group, a lower alkylthio group, a lower alkylsulfonyl group, an ethyl group substituted with a phenoxy group which may be substituted with one or two lower alkyl groups, a glycidyl group, an acetonyl group, a dioxoranyl group substituted with a phenoxymethyl group which may be substituted with a chlorine atom, a 2,2-diethoxyethyl group, a 1-ethoxycarbonylethyl group, a trimethylsilylmethyl group, a 1-pyridylethyl group, a lower alkyl group substituted with a benzylimino group which may be substituted with a lower alkoxyimino group or a lower alkyl group.

As understood from the above formula (I), the compounds of the present invention have amino groups and easily form acid addition salts. Such salts are also included in the present invention.

Acids capable of forming salts may include inorganic acids such as a hydrochloric acid, a hydrobromic acid, a nitric acid, a sulfuric acid and a phosphoric acid; carboxylic acids such as a formic acid, an oxalic acid, a fumatic acid, an adipic acid, a stearic acid, an oleic acid and an aconitic acid, and organic sulfonic acids such as a methanesulfonic acid, a benzenesulfonic acid and a p-toluenesulfonic acid.

In the above formula (I), when any of carbon atoms is an asymmetric carbon atom, its optical isomers and racemic compound or mixture thereof are all included in the present invention.

The compound (I) of the present invention can be easily prepared according to the process shown below, which are know per se in the art.

PREPARATION PROCESS A

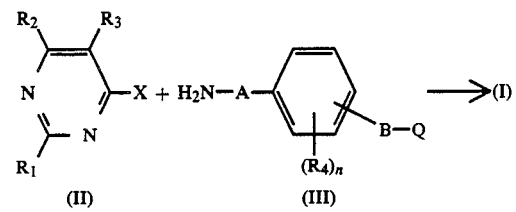

wherein $R_1$, $R_2$, $R_3$, $R_4$, n, A, B and Q are as defined above; and X represents an eliminatable group.

As described above, the reaction itself is known in the art. Therefore, the eliminatable group X is not limited at all, and includes halogen atoms such as a chlorine atom, a bromine atom or an iodine atom; alkylthio groups such as a methylthio group, an ethylthio group, a propylthio group and a butylthio group; alkanesulfonyloxy groups which may be substituted with a halogen atom such as a methanesulfonyloxy group, an ethanesulfonyloxy group and a trifluoromethanesulfonyloxy group; arenesulfonyloxy groups such as a benzenesulfonyloxy group and a p-toluenesulfonyloxy group; and a hydroxyl group.

As clearly seen from the reaction scheme shown above, the compound H—X is eliminated in the reaction. For capturing the eliminated compound and allowing the reaction to proceed smoothly, the reaction is preferably carried out in the presence of a base. In general, the reaction is carried out in the presence of a solvent, but can be also carried out heating and melting the compounds of the formula (II) and the formula (III) under solvent-free conditions.

The solvent is not particularly limited as long as it does not participate in the above reaction and may include aromatic, aliphatic and alicyclic hydrocarbons which are chlorinated or not chlorinated, such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, ethylene glycol dimethyl ether, tetrahydrofuran and dioxane; ketones such as acetone and methyl ethyl ketone; alcohols such as methanol, ethanol and ethylene glycol, or hydrates thereof; amides such as N,N-dimethylformamide (DMF) and N,N-dimethylacetamide; organic bases such as pyridine and N,N-diethylaniline; and mixtures of the solvents described above.

The base may include organic bases such as triethylamine, pyridine and N,N-diethylaniline, alkali metal alkoxides such as sodium methoxide and sodium ethoxide, and inorganic bases such as sodium hydride, sodium amide, sodium hydroxide, potassium hydroxide, sodium carbonate and potassium carbonate.

The reaction temperature is not particularly limited but generally from room temperature to the boiling point of the solvent used. Heating should preferably be carried out for shortening the reaction time.

PREPARATION PROCESS B

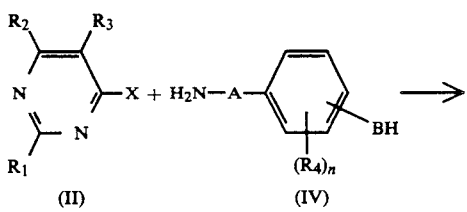

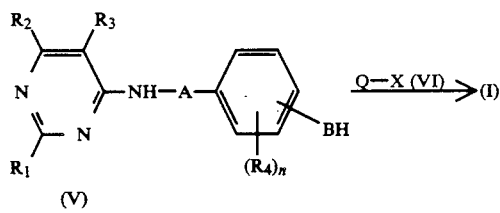

wherein $R_1$, $R_2$, $R_3$, $R_4$, n, A, B, Q and X are as defined above.

In the above process, the intermediate (V) is synthesized and then, allowed to react with the compound Q—X (VI). The same solvent, base, etc. may suitably be employed as those described in the above-mentioned Preparation process A.

PREPARATION PROCESS C

In the above formula (I), the compound in which $R_2$ is a lower alkyl group substituted with a lower alkoxy group or a lower alkylthio group, can be also prepared according to the process shown below.

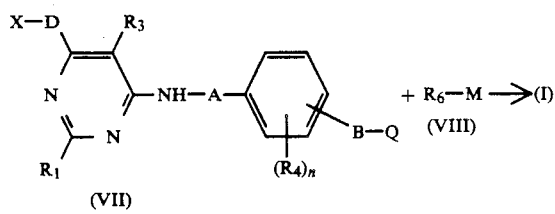

wherein $R_1$, $R_3$, $R_4$, n, A, B, Q and X are as defined above; D represents a lower alkylene group; $R_6$ represents a lower alkoxy group or a lower alkylthio group; and M represents an alkali metal, preferably sodium.

PREPARATION PROCESS D

In the above formula (I), the compound in which Q is a compound which is identical to the group

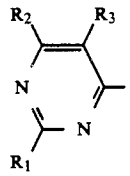

can be also prepared according to the method shown below.

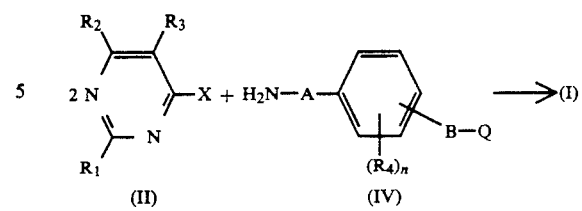

wherein $R_1$, $R_2$, $R_3$, $R_4$, n, A, B, Q and X are as defined above.

As the solvent, the base, etc. used in the above process, there may suitably be employed those described in the above-mentioned Preparation process A.

PREPARATION PROCESS E

In the above formula (I″), the compound in which Q is an alkyl group substituted with a benzylimino group which may be substituted with a lower alkoxyimino group or a lower alkyl group can be also prepared according to the method shown below:

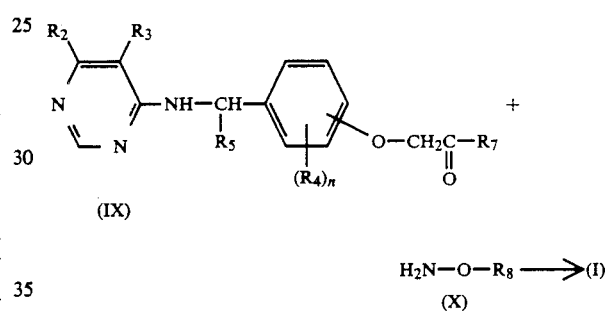

wherein $R_2$, $R_3$, $R_4$, $R_5$ and n are as defined above; $R_7$ represents a hydrogen atom or a lower alkyl group; and $R_8$ represents a lower alkyl group or a benzyl group which may be substituted with a lower alkyl group.

PREPARATION PROCESS F

In the above formula (I″), the compound in which Q is a 1,3-dioxoran-2-yl-methyl group can be also prepared according to the method shown below:

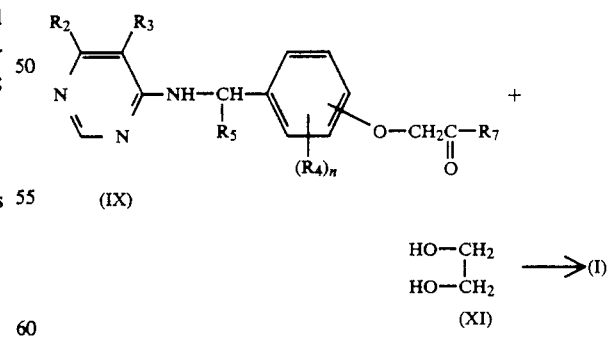

wherein $R_2$, $R_3$, $R_4$, $R_5$ and n are as defined above; and $R_7$ represents a hydrogen atom.

PREPARATION PROCESS G

In the above formula (I″), the compound in which Q is a 2,2-difluoropropyl group can be also prepared according to the method shown below:

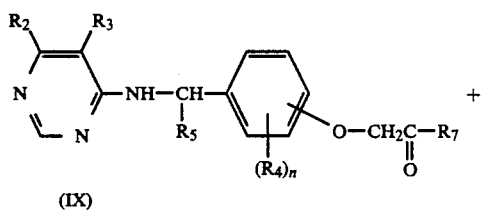

(IX)

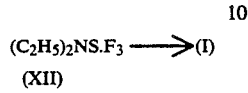

wherein $R_2$, $R_3$, $R_4$, $R_5$ and n are as defined above; and $R_7$ represents a methyl group.

In the Preparation processes A, B and D described above, among the compounds of the formulae (III) and (IV) to be used as the starting material, the compound in which the chain member of the lower alkylene group represented by A is one and is mono-substituted, may be prepared according to the process shown below, which is known per se in the art.

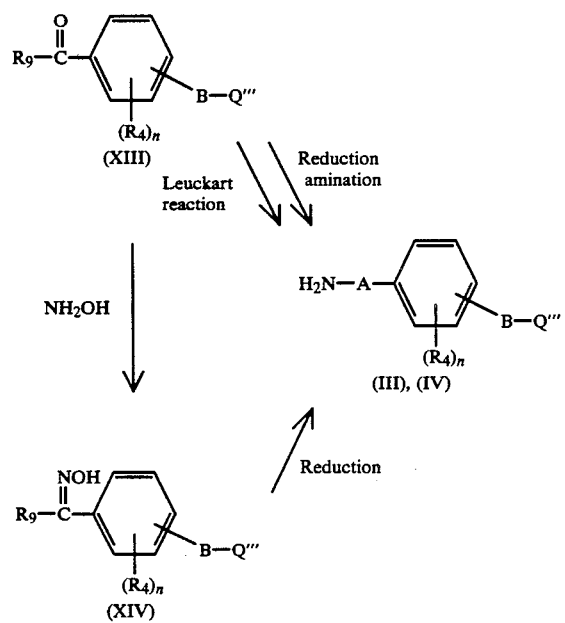

wherein $R_4$, n, A and B are as defined above; $R_9$ represents a cycloalkyl group having 3 to 5 carbon atoms, a lower alkynyl group, or a lower alkyl group which is unsubstituted or substituted with a halogen atom, a lower alkoxy group or a lower alkylthio group; and $Q'''$ is as defined above for Q or a hydrogen atom.

Among the compounds of the formula (III), the compound in which the chain member of the lower alkylene group represented by A has 2 to 5 carbon atoms, may be prepared, for example, according to the process shown below, which is known per se in the art.

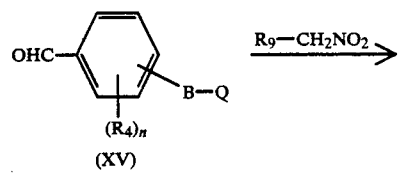

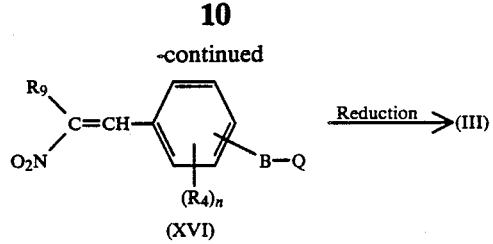

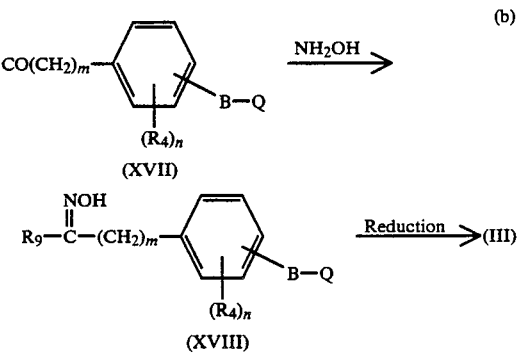

wherein $R_4$, $R_9$, n, and Q are as defined above; and m is an integer of 1 to 4.

Further, among the compounds of the formula (III), the compound in which A is di-substituted, may be prepared, for example, according to the process shown below, which is known per se in the art.

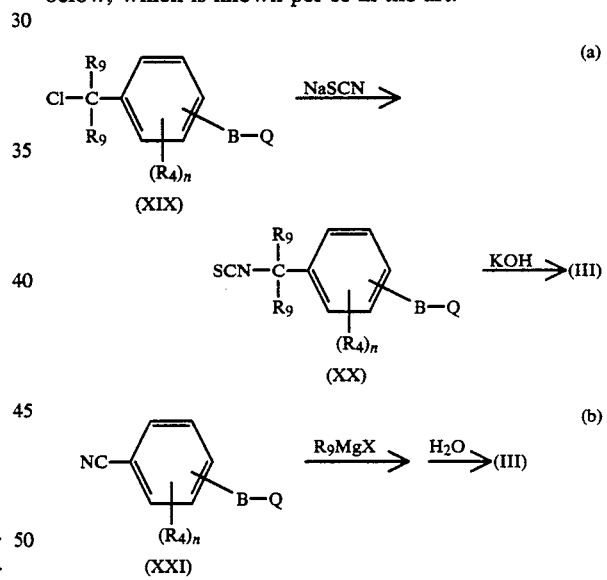

wherein $R_4$, $R_9$, n, B and Q are as defined above.

Further, the compounds (III) and (IV) can also be prepared by Hoffmann decomposition of corresponding acid amides.

The desired product (I) obtained according to the respective processes as described above can be purified suitably by known means such as recrystallization, various chromatographies, etc.

The acid addition salt can be obtained easily by, for example, introducing an acid into the reaction mixture after completion of the reaction and then removing the solvent.

The compounds of the present invention exhibit excellent effects against Hemiptera such as planthoppers, leafhoppers, aphids, white flys, etc.; Leipdoptera such as cabbage armworms, diamondback moth, leaf roller moths, pyralic moths, stem-borers, common white, etc.; Coleoptera such as weevils, leaf beetles, etc.; and other agricultural and horticultural injurious insects, for example, Acarina such as citrus red mite, two-spotted spider mite, etc. Also, they are very effective for prevention and extermination of hygienically injurious insects such as fly, mosquito, cockroach, etc., and also effective for other injurious insects against stored crops.

Further, the compounds of the present invention have also activities against root-knot nematode, pine wood nematode, bulb mite in the soil. Also, the compounds of the present invention are effective and active against diseases for agriculture and horticulture such as blast, powdery mildew, and otherwise downy mildew, late blight, etc.

Thus, the uses and application fields of the compounds of the present invention are very wide, and therefore they can be provided for practical application in various dosage forms with high activities. The insecticide, the acaricide and the fungicide of the present invention may comprise one or several kinds of the compounds of the formula (I). Although the compound of the formula (I) may be used per se, it is generally formulated with common carriers, surfactants, dispersing agent or auxiliary agents, and prepared in a conventional manner into compositions such as powder, wettable powder, emulsion, fine granule, granule, aqueous or oily suspension, aerosol, etc. before use.

Suitable carriers may include, for example, solid carriers such as talc, bentonite, clay, kaolin, diatomaceous earth, white carbon, vermicullite, slaked lime, siliceous sand, ammonium sulfate, urea, etc.; liquid carriers, for example, hydrocarbons such as kerosene, mineral oil, etc.; aromatic hydrocarbons such as benzene, toluene, xylene, etc.; chlorinated hydrocarbons such as chloroform, carbon tetrachloride, etc.; ethers such as dioxane, tetrahydrofuran, etc.; ketones such as acetone, cyclohexanone, isophorone, etc.; esters such as ethyl acetate, ethylene glycol acetate, dibutyl maleate, etc.; alcohols such as methanol, n-hexanol, ethylene glycol, etc.; polar solvents such as dimethylformamide, dimethyl sulfoxide, etc.; or water. Also, as gaseous carrier, air, nitrogen, carbon dioxide, Freon, etc. can be used to effect mixed jetting.

Also, as the surfactant, the dispersing agent for improvement of attachment or absorption of the present agent onto animals and vegetables or for improvement of performances of dispersion, emulsification or spreading of the medicine, there may be employed, for example, alcohol sulfate esters, alkyl sulfonate salts, lignin sulfonate salts, polyoxyethylene glycol ethers, etc.

Further, for amelioration of the properties of the preparation, as the auxiliary agent, for example, carboxymethyl cellulose, polyethylene glycol, gum arabic, etc. may be employed.

The above carrier, surfactant, dispersing agent and auxiliary agent may be used either individually or in combination depending on the respective purposes The active ingredient concentration when the compound of the present invention is formed into a preparation may be generally 1 to 50% by weight for emulsion, generally 0.3 to 25% by weight for powder, generally 1 to 90% by weight for wettable powder, generally 0.5 to 5% by weight for granule, generally 0.5 to 5% by weight for oil and generally 0.1 to 5% by weight for aerosol.

These preparations can be diluted to appropriate concentrations, and provided for various uses depending on the respective purposes, such as by spraying onto stalks or leaves of vegetables, the surface of soil or paddy field, or alternatively by direct application.

EXAMPLES

The present invention is described below in more detail by referring to Examples, by which the present invention is not limited at all.

EXAMPLE 1

Synthesis of dl-5-chloro-6-ethyl-4-(α-ethyl-3-phenoxybenzyl)aminopyrimidine (Compound No. 3)

To a solution of 1.8 g of 4,5-dichloro-6-ethylpyrimidine dissolved in 50 ml of toluene were added 1.1 g of triethylamine and 2.2 g of α-ethyl-3-phenoxybenzylamine, and the mixture was refluxed under stirring for 6 hours. After completion of the reaction, the product was washed with water, dried over anhydrous sodium sulfate and the solvent was distilled off under reduced pressure. The oily product obtained was isolated by chromatography (Wako Gel C-200, trade name, eluted with toluene: ethyl acetate=7:1) to give 2.0 g of the desired product as pale yellow oily liquid.
$n_D^{21.2}$ 1.5818.

EXAMPLE 2

Synthesis of dl 5-chloro-6-ethyl-4-[α-ethyl-4-(4-fluorophenoxy)benzyl]aminopyrimidine (Compound No. 41)

To a solution of 1.8 g of 4,5-dichloro-6-ethylpyrimidine dissolved in 50 ml of toluene were added 1.1 g of triethylamine and 2.6 g of α-ethyl-4-(4-fluorophenoxy)benzylamine, and the mixture was refluxed under stirring for 6 hours. After completion of the reaction, the triethylamine hydrochloride formed was filtered off, and from the filtrate, the solvent was distilled off under reduced pressure. The oily product obtained was isolated by chromatography (Wako Gel C-200, trade name, eluted with toluene: ethyl acetate =7:1) to give 1.8 g of the desired product as pale yellow oily liquid.
$n_D^{21.6}$ 1.5694.

EXAMPLE b 3

Synthesis of dl-5-chloro-6-ethyl-4-(α-isopropyl-4-phenoxy)benzyl]aminopyrimidine (Compound No. 22)

To a solution of 1.8 g of 4,5-dichloro-6-ethylpyrimidine dissolved in 50 ml of xylene were added 1.1 g of triethylamine and 2.4 g of α-isopropyl-4-phenoxybenzylamine, and the mixture was refluxed under stirring for 7 hours. After completion of the reaction, the product was washed with water, dried over anhydrous sodium sulfate and the solvent was distilled off under reduced pressure. The oily product obtained was isolated by chromatography (Wako Gel C-200, trade name, eluted with toluene: ethyl acetate=7:1) to give 2.1 g of the desired product as pale yellow oily liquid.
$n_D^{23.0}$ 1.5823.

EXAMPLE 4

Synthesis of dl-5-chloro-6-chloromethyl-4-(α-ethyl-3-phenoxybenzy))aminopyrimidine (Compound No. 10)

To a solution of 2.1 g of 6-chloromethyl-4,5-dichloropyrimidine dissolved in 50 ml of toluene were added 1.0 g of triethylamine and 2.2 g of α-ethyl-3-phenoxybenzylamine, and the mixture was stirred at 50° to 60° C. for 3 hours. After completion of the reaction, the triethylamine hydrochloride formed was filtered off, and from the filtrate, the solvent was distilled off under reduced pressure. The oily product obtained was isolated by chromatography (Wako Gel C-200, trade name, eluted with toluene:ethyl acetate=5:1) to give 2.8 g of the desired product as pale yellow oily liquid. $n_D^{27.6}$ 27.6

EXAMPLE 5

Synthesis of dl-5-chloro-4-(α-ethyl-3-phenoxybenzylamino)-6-methylthiomethylpyrimidine (Compound No. 12)

To a solution of 2.0 g of dl-5-chloro-6-chloromethyl-4-(α-ethyl-3-phenoxybenzyl)aminopyrimidine obtained in Example 4 dissolved in 50 ml of methanol was added 10 ml of a 15% aqueous methanthiol sodium salt solution, and the mixture was refluxed under stirring for 2 hours. After completion of the reaction, the product was poured into water and extracted with ethyl acetate. The extract was washed with water, dried over anhydrous sodium sulfate and the solvent was distilled off under reduced pressure. The oily product obtained was isolated by chromatography (Wako Gel C-200, trade name, eluted with toluene:ethyl acetate=5:1) to give 1.8 g of the desired product as pale yellow oily liquid. $n_D^{27.6}$ 1.6014.

EXAMPLE 6

Synthesis of dl-5-chloro-6-ethyl-4-(α-ethyl-3-phenoxybenzyl)aminopyrimidine.oxalate In 20 ml of acetone were dissolved 0.61 g of dl-5-chloro-6-ethyl-4-(αethyl-3-phenoxybenzyl)aminopyrimidine obtained in Example 1 and 0.15 g of oxalic acid, and the mixture was refluxed under heating for 1 hour. After completion of the reaction, the solvent was distilled off under reduced pressure, and then washed with n-hexane to give 0.7 g of the desired product as a colorless viscous product.

EXAMPLE 7

Synthesis of dl-5-chloro-6-ethyl-4-[α-ethyl-4-(4-fluorophenoxy)benzyl[aminopyrimidine hydrochloride In 20 ml of anhydrous ether was dissolved 1.0 g of dl-5-chloro-6ethyl-4-[αethyl-4-(4-fluorophenoxy)benzyl]aminopyrimidine obtained in Example 2 and the dried hydrochloric acid gas was blown into the mixture. Ether was removed from the separated oily product, and the product obtained was washed with n-hexane to give 1.0 g of the desired product as a colorless viscous product.

EXAMPLE 8

The procedures were carried out in the same manner as in Examples 1 to 5 to give compounds indicated as Compounds Nos. 1, 2, 4 to 9, 11, 13 to 21, 32 to 40 to 42 to 65 shown in Table 1.

EXAMPLE 9

Synthesis of dl-5-chloro-6-ethyl-4-[α-ethyl-4-(5-nitropyridin-2-yloxy)benzyl]aminopyrimidine (Compound No. 78)

To a solution of 0.9 g of 4,5-dichloro-6-ethylpyrimidine dissolved in 30 ml of toluene were added 0.6 g of triethylamine and 1.3 g of α-ethyl-4-(5-nitropyridin-2-yloxy)benzylamine, and the mixture was refluxed under heating and stirring for 12 hours. After completion of the reaction, the product was extracted with ethyl acetate, washed with water and dried over anhydrous sodium sulfate. Then, the solvent was distilled off under reduced pressure, and the oily product obtained was isolated by chromatography (Wako Gel C-200, trade name, eluted with toluene:ethyl acetate=2:1) to give 0.8 g of the desired product as colorless oily liquid. $n_D^{22.2}$ 1.5962.

EXAMPLE 10

Synthesis of dl-5-chloro-6-ethyl-4-[α-ethyl-4-(3-pyridyloxy)benzyl]aminopyrimidine (Compound No. 72)

To a solution of 2.2 g of dl-5-chloro-6-ethyl-4-(α-ethyl-4-hydroxybenzyl)aminopyrimidine sodium salt dissolved in 25 ml of dried pyridine were added 1.1 g of 3-bromopyridine and 1 g of cuprous chloride, and the mixture was refluxed under nitrogen atmosphere by heating and stirring for 8 hours. After completion of the reaction, the reaction product was poured into water and extracted with ethyl acetate. The extract was washed with diluted hydrochloric acid and water, dried over anhydrous sodium sulfate and the solvent was distilled off under reduced pressure The oily product obtained was isolated by chromatography (Wako Gel C-200, trade name, eluted with toluene:ethyl acetate=4 : 1) to give 0.8 g of the desired product as colorless oily liquid. $n_D^{20.5}$ 1.5974.

EXAMPLE 11

Synthesis of dl-5-chloro-6-ethyl-4-[α-ethyl-4-(2-pyrimidyloxy)benzyl]aminopyrimidine (Compound No. 88)

To a solution of 0.9 g of 4,5-dichloro-6-ethyl-4-(α-ethyl-4-hydroxybenzyl)aminopyrimidine dissolved in 30 ml of DMF were added 0.45 g of 2-chloropyrimidine and 0.7 g of anhydrous potassium carbonate, and the mixture was heated to about 100° C. for 12 hours under stirring. After completion of the reaction, the reaction product was poured into ice-cold water and extracted with ethyl acetate. The extract was washed with water, dried over anhydrous sodium sulfate, and the solvent was distilled off under reduced pressure. The residue was isolated by column chromatography (Wako Gel C-200, trade name, eluted with toluene:ethyl acetate=3:1) to give 0.7 g of the desired product as colorless crystals.
m.p.: 100° to 112° C.

EXAMPLE 12

Synthesis of dl-5-chloro-6-ethyl-4-[α-ethyl-4-(5-chloro-6-ethyl-pyrimidin-4-yloxy)benzyl]aminopyrimidine (Compound No. 82)

To a solution of 4.5 g of 4,5-dichloro-6-ethylpyrimidine dissolved in 30 ml of toluene were added 4 g of triethylamine and 1.3 g of α-ethyl-4-hydroxybenzylamine, and the mixture was refluxed under stirring for 24 hours. After completion of the reaction, the reaction product was extracted with ethyl acetate, washed with water, dried over anhydrous sodium sulfate and the solvent was distilled off under reduced pressure. The oily product obtained was isolated by column chromatography (Wako Gel C-200, trade name, eluted with toluene:ethyl acetate=3:1) to give 0.8 g of the desired product as colorless oily liquid.

$n_D^{23.5}$ 1.5738.

EXAMPLE 13

The procedures were carried out in the same manner as in Examples 9 to 12 to give compounds indicated as Compounds Nos. 66 to 71, 73 to 77, 79 to 81, 83 to 97 and 89 to 95 shown in Table 1.

TABLE 1

[Structure: pyrimidine with $R_1$, $R_2$, $R_3$ substituents connected via —NH—A— to a phenyl ring with $R_4$ and —B—Q substituents]

| Compound No. | $R_1$ | $R_2$ | $R_3$ | A | $R_4$ | —B—Q | Physical property |
|---|---|---|---|---|---|---|---|
| 1 | H | $CH_3$ | Cl | —CH($C_2H_5$)— | H | | $n_D^{21.2}$ 1.5938 |
| 2 | | | F | | | | $n_D^{26.8}$ 1.5850 |
| 3 | | $C_2H_5$ | Cl | | | 3-O-phenyl | $n_D^{21.2}$ 1.5918 |
| 4 | | n-$C_3H_7$ | | | | | $n_D^{25.0}$ 1.5534 |
| 5 | | i-$C_3H_7$ | | | | | $n_D^{25.2}$ 1.5763 |
| 6 | | Cl | | | | | $n_D^{24.2}$ 1.6022 |
| 7 | | | Br | | | | $n_D^{22.4}$ 1.6102 |
| 8 | | Br | Cl | | | | $n_D^{26.8}$ 1.6142 |
| 9 | | | Br | | | | $n_D^{23.3}$ 1.6333 |
| 10 | | $ClCH_2$— | Cl | | | | $n_D^{27.6}$ 1.5965 |
| 11 | H | $CH_3OCH_2$— | Cl | —CH($C_2H_5$)— | H | | $n_D^{27.6}$ 1.5895 |
| 12 | | $CH_3SCH_2$— | | | | | $n_D^{27.6}$ 1.6014 |
| 13 | | $FCH_2$— | | | | 3-O-phenyl | $n_D^{22.7}$ 1.5971 |
| 14 | $CH_3$ | $C_2H_5$ | | | | | $n_D^{25.2}$ 1.5795 |
| 15 | $CCl_3$ | | | | | | $n_D^{26.0}$ 1.5805 |
| 16 | $ClCH_2$— | | | | | | $n_D^{26.0}$ 15626 |
| 17 | H | | Br | —CH($CH_3$)— | | 4-O-phenyl-F | $n_D^{28.6}$ 1.5959 |
| 18 | | | Cl | | | 3-O-phenyl | $n_D^{21.4}$ 1.5994 |
| 19 | | | | —CH($C_2H_5$)— | | | $n_D^{21.4}$ 1.5995 |
| 20 | | | | —CH(n-$C_3H_7$)— | | | $n_D^{21.4}$ 1.5924 |
| 21 | | | | —CH(n-$C_3H_7$)— | | 4-O-phenyl | $n_D^{22.8}$ 1.5811 |
| 22 | | | | —CH(i-$C_3H_7$)— | | | $n_D^{23.0}$ 1.5823 |
| 23 | | | | —CH(n-$C_5H_{11}$)— | | | $n_D^{25.8}$ 1.5686 |
| 24 | | | | —CH(cyclopropyl)— | | | $n_D^{21.5}$ 1.5904 |
| 25 | H | $C_2H_5$ | Cl | —CH($CF_3$)— | H | | Note 1 |
| 26 | | | | —CH($CH_2SCH_3$)— | | | $n_D^{26.8}$ 1.5826 |
| 27 | | | | —C($CH_3$)$_2$— | | 4-O-phenyl | $n_D^{24.0}$ 1.5969 |
| 28 | | | | —C($CH_3$)($C_2H_5$)— | | | Note 2 |
| 29 | | | | —CH($C_2H_5$)—$CH_2$— | | | $n_D^{21.6}$ 1.5853 |
| 30 | | | | —CH($C_2H_5$)—$CH_2CH_2$— | | | $n_D^{24.8}$ 1.5792 |
| 31 | | | | —C($CH_3$)$_2$— | | 3-O-phenyl | Note 3 |

TABLE 1-continued
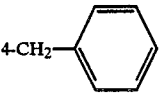
| Compound No. | R₁ | R₂ | R₃ | A | R₄ | —B—Q | Physical property |
|---|---|---|---|---|---|---|---|
| 32 | | | | —CH(C₂H₅)— | | 4-CH₂—C₆H₅ | $n_D^{19.4}$ 1.5929 |
| 33 | | | | —CH(CH₃)— | | 3-OCH₂—C₆H₅ | $n_D^{19.0}$ 1.5962 |
| 34 | | | | —CH(C₂H₅)— | | 4—C₆H₅ | $n_D^{22.0}$ 1.6070 |
| 35 | H | C₂H₅ | Cl | —CH(C₂H₅)— | H | 3-O—C₆H₄—O—C₆H₅ | $n_D^{21.8}$ 1.6023 |
| 36 | | | | | | 3-O—C₆H₄(2-CH₃) | $n_D^{23.7}$ 1.5822 |
| 37 | | | | | | 3-O—C₆H₄-4-F | $n_D^{20.4}$ 1.5825 |
| 38 | | | | | | 3-O—C₆H₄-4-Cl | $n_D^{22.2}$ 1.5953 |
| 39 | | | | | | 3-O—C₆H₄-4-CH₃ | $n_D^{21.6}$ 1.5840 |
| 40 | | | | | | 3-O—C₆H₄-4-OC₄H₉-n | $n_D^{25.7}$ 1.5716 |
| 41 | | | | | | 4-O—C₆H₄-4-F | m.p. 64 to 65 °C. |
| 42 | | | | | | 3-O—C₆H₄-4-C(CH₃)₃ | $n_D^{25.2}$ 1.5752 |

TABLE 1-continued
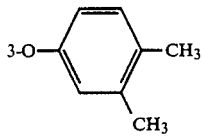
| Compound No. | R₁ | R₂ | R₃ | A | R₄ | —B—Q | Physical property |
|---|---|---|---|---|---|---|---|
| 43 | H | C₂H₅ | Cl | —CH(C₂H₅)— | H | 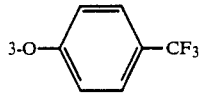 3-O—⟨⟩—CH₃ (with CH₃) | $n_D^{25.2}$ 1.5878 |
| 44 | | | | | | 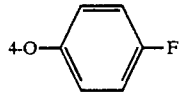 3-O—⟨⟩—CF₃ | m.p. 98–99.5° C. |
| 45 | | | | —CH(CH₃)— | | 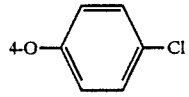 4-O—⟨⟩—F | $n_D^{26.2}$ 1.5760 |
| 46 | | | | —CH(C₂H₅)— | | 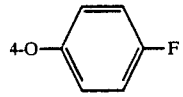 4-O—⟨⟩—Cl | m.p. 104–105° C. |
| 47 | | | | —CH(i-C₃H₇)— | | | $n_D^{24.2}$ 1.5905 |
| 48 | | | | | | | $n_D^{24.2}$ 1.5846 |
| 49 | | | | | | 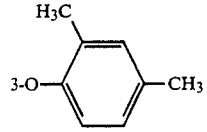 4-O—⟨⟩—F | $n_D^{26.2}$ 1.5644 |
| 50 | | | | —CH(C₂H₅)— | | 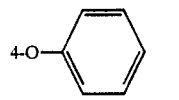 3-O—⟨⟩—CH₃ (with H₃C) | $n_D^{25.7}$ 1.5732 |
| 51 | | | | —CH(CH₃)— | 3-CH₃ | 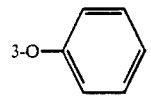 4-O—⟨⟩ | m.p. 77–78° C. |
| 52 | | | | | 3-Cl | | — |
| 53 | H | C₂H₅ | CH₃ | —CH(C₂H₅)— | H | 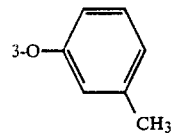 3-O—⟨⟩ | $n_D^{25.0}$ 1.5892 |
| 54 | | | Cl | | | 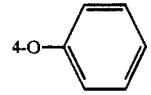 3-O—⟨⟩—CH₃ | $n_D^{25.2}$ 1.5765 |
| 55 | | | | —CH(t-C₄H₉)— | | 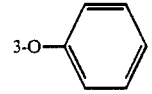 4-O—⟨⟩ | $n_D^{24.0}$ 1.5678 |
| 56 | | | Cl | —CH(C₂H₅)—(CH₂)₃— | | 3-O—⟨⟩ | Note 4 |

TABLE 1-continued

Structure:

$$\text{Pyrimidine with } R_1, R_2, R_3 \text{ substituents} - NH - A - \text{phenyl}(R_4) - B - Q$$

| Compound No. | R₁ | R₂ | R₃ | A | R₄ | —B—Q | Physical property |
|---|---|---|---|---|---|---|---|
| 57 | | | | —CH(C₂H₅)— | | 4-CH(CH₃)–phenyl | $n_D^{23.0}$ 1.5807 |
| 58 | | | | —CH(C≡CH)— | | 4-O–phenyl | — |
| 59 | | | | —CH(C₂H₅)— | 4-F | 3-O–phenyl | — |
| 60 | H | C₂H₅ | Cl | —CH(C₂H₅)— | H | 4-O–(4-CH₃-phenyl) | m.p. 63–64° C. |
| 61 | | | | —CH(i-C₃H₇)— | | 4-O–(4-CH₃-phenyl) | $n_D^{29.8}$ 1.5730 |
| 62 | | | | —CH(C₂H₅)— | | 4-O–(4-OCH₃-phenyl) | $n_D^{30.7}$ 1.5881 |
| 63 | | | | —CH(i-C₃H₇)— | | 4-O–(4-OCH₃-phenyl) | $n_D^{30.5}$ 1.5752 |
| 64 | | | | —CH(cyclopropyl)— | | 4-O–(4-F-phenyl) | m.p. 58.5–60° C. |
| 65 | | | | | | 4-O–(4-Cl-phenyl) | m.p. 90–91.5° C. |
| 66 | | Cl | CH₃ | —CH(C₂H₅)— | | 4-O–(5-Cl-6-C₂H₅-pyrimidin-4-yl) | $n_D^{24.4}$ 1.5973 |
| 67 | | | | | | 4-O–(5-CH₃-6-Cl-pyrimidin-4-yl) | $n_D^{24.8}$ 1.6067 |
| 68 | H | C₂H₅ | Cl | —CH(CH₃)— | H | 4-O–(5-Cl-6-C₂H₅-pyrimidin-4-yl) | $n_D^{19.4}$ 1.5832 |
| 69 | | | | —CH(i-C₃H₇)— | | | $n_D^{22.4}$ 1.5661 |
| 70 | | | | —CH(n-C₅H₁₁)— | | | $n_D^{22.8}$ 1.5968 |

TABLE 1-continued

[Structure: pyrimidine-NH-A-phenyl(R4)-B-Q with R1, R2, R3 substituents]

| Compound No. | R1 | R2 | R3 | A | R4 | —B—Q | Physical property |
|---|---|---|---|---|---|---|---|
| 71 | | | | —CH(C₂H₅)— | | 4-[pyridine] | $n_D^{24.2}$ 1.5970 |
| 72 | | | | | | 4-O-[pyridine] | $n_D^{20.5}$ 1.5974 |
| 73 | | | | | | 4-O-[pyridine] | m.p. 101–102° C. |
| 74 | | | | | | 4-O-[pyridine-CF₃] | m.p. 104–106° C. |
| 75 | | | | | | 4-O-[pyridine-Cl] | m.p. 90–92° C. |
| 76 | H | C₂H₅ | Cl | —CH(C₂H₅)— | H | 4-O-[pyridine-Cl] | $n_D^{23.0}$ 1.5824 |
| 77 | | | | | | 4-O-[pyridine-CF₃, Cl] | $n_D^{24.8}$ 1.5469 |
| 78 | | | | | | 4-O-[pyridine-NO₂] | $n_D^{22.2}$ 1.5962 |
| 79 | | | | | | 4-O-[pyridine-OCH₃] | $n_D^{26.2}$ 1.5613 |
| 80 | | | | | | 4-O-[pyridine-Cl] | $n_D^{21.2}$ 1.9856 |

TABLE 1-continued
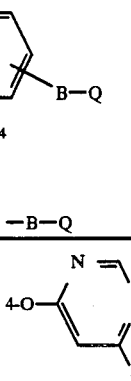
| Compound No. | $R_1$ | $R_2$ | $R_3$ | A | $R_4$ | —B—Q | Physical property |
|---|---|---|---|---|---|---|---|
| 81 | | | | | | 4-O—[pyrimidine with Cl] | $n_D^{22.8}$ 1.5968 |
| 82 | H | $C_2H_5$ | Cl | —CH($C_2H_5$)— | H | 4-O—[pyrimidine with Cl, $C_2H_5$] | m.p. 83–85° C. |
| 83 | | | | | | 4-O—[pyrimidine with Cl, $CH_3$] | m.p. 106–108° C. |
| 84 | | | | | | 4-O—[pyrimidine with $H_3C$, Cl] | $n_D^{27.2}$ 1.5706 |
| 85 | | | | | | 4-O—[pyrimidine with $CCl_3$, Cl, $C_2H_5$] | $n_D^{27.2}$ 1.5642 |
| 86 | | | | | | 4-O—[pyrimidine with $SCH_3$, F, $CH_3$] | $n_D^{27.2}$ 1.5684 |
| 87 | | | | | | 4-O—[pyrimidine] | $n_D^{19.6}$ 1.5796 |
| 88 | H | $C_2H_5$ | Cl | —CH($C_2H_5$)— | H | 4-O—[pyrimidine] | m.p. 110–112° C. |
| 89 | | | | | | 4-O—[pyrazine] | m.p. 95–96° C. |

TABLE 1-continued

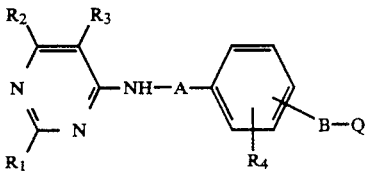

| Compound No. | R₁ | R₂ | R₃ | A | R₄ | —B—Q | Physical property |
|---|---|---|---|---|---|---|---|
| 90 | | | | | | 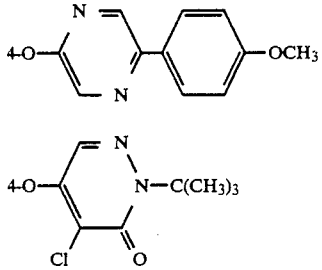 | Glass-like Note 5 |
| 91 | | | | | | 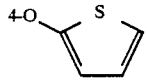 | Glass-like Note 6 |
| 92 | | | | | | 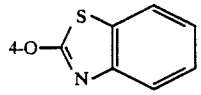 | Glass-like Note 7 |
| 93 | | | | | | 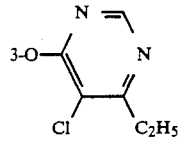 | $n_D^{19.5}$ 1.6156 |
| 94 | | | | | | 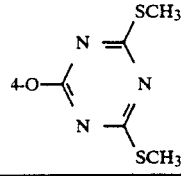 | $n_D^{23.0}$ 1.5832 |
| 95 | H | C₂H₅ | Cl | —CH(C₂H₅)— | H | (4-O—pyrimidine with 2,6-bis-SCH₃) | $n_D^{25.0}$ 1.6032 |

Note 1 PMR (δppm, CDCl3): 1.27 (3H, t), 2.82 (2H,d), 5.90–6.13 (2H, m), 6.98–7.45 (9H, m), 8.45 (1H, s).
Note 2 PMR (δppm, CDCl3): 0.85 (3H, t), 1.28 (3H, t), 1.82 (3H, t), 1.90–2.30 (2H, m), 2.79 (2H, q), 5.75 (1H, s), 6.90–7.38 (9H, m), 8.23 (1H, s).
Note 3 PMR (δppm, CDCl3): 1.26 (3H, t), 1.80 (6H, s), 1.78 (2H, q), 5.73 (1H, s), 6.80–7.33 (9H, m), 8.24 (1H, s).
Note 4 PMR (δppm, CDCl3): 0.90 (3H, t), 1.26 (3H, t), 1.40–1.95 (6H, m), 2.57–2.88 (4H, m), 4.20 (1H, d), 5.20 (1H, d), 6.80–7.90 (9H, m), 8.35 (1H, s).
Note 5 PMR (δppm, CDCl3): 0.99 (3H, t), 1.27 (3H, t), 1.97 (2H, 8), 2.81 (2H, q), 3.88 (3H, s), 5.19 (1H, m), 5.62 (1H, br), 7.01 (2H, d), 7.16 (2H, d), 7.42 (2H,d), 7.87 (2H, d), 8.38–8.48 (3H, m).
Note 6 PMR (δppm, CDCl3): 0.97 (3H, t), 1.26 (3H, t), 1.63 (9H, s), 1.93 (2H, q), 2.79 (2H, q), 5.15 (1H, m), 5.62 (1H, br), 7.07 (2H, d), 7.36–7.43 (3H, m), 8.38 (1H, s).
Note 7 PMR (δppm, CDCl3): 0.96 (3H, t), 1.25 (3H, t), 1.86–2.02 (2H, m), 2.79 (2H, q), 5.12 (1H, m), 5.59 (1H, br), 6.54–7.31 (7H, m), 8.38 (1H, s).

EXAMPLE 14

Synthesis of dl-5-chloro-6-ethyl-4-α-ethyl-4-(isoamyloxy)-benzyl]aminopyrimidine (Compound No. 102)

To a solution of 1.5 g of dl-α-ethyl-4-(3-methylbutoxy)benzylamine and 1.5 g of 4,5-dichloro-6-ethylpyrimidine dissolved in 40 ml of toluene was added 1.2 g of triethylamine, and the mixture was refluxed by heating for 8 hours under stirring. After completion of the reaction, the solvent was distilled off under reduced pressure. The residue was isolated by column chromatography (Wako Gel C-200, trade name, eluted with toluene-:ethyl acetate=7:1) to give 1.1 g of the desired product as pale yellow liquid.

$n_D^{17.2}$ 1.5444.

EXAMPLE 15

Synthesis of dl-5-chloro-6-ethyl-4-[α-ethyl-4-(sec-amyloxy)benzyl]aminopyrimidine (Compound No. 103)

To a solution of 1.1 g of dl-5-chloro-6-ethyl-4-(α-ethyl-4-hydroxybenzyl)aminopyrimidine sodium salt dissolved in 30 ml of N,N-dimethylformamide was added 0.6 g of 2-bromopentane, and the mixture was stirred at 90° to 100° C. for 8 hours. After completion of the reaction, the reaction mixture was poured into water and separated oily product was extracted with ethyl acetate. The extract was washed with water, dried over anhydrous sodium sulfate and ethyl acetate was distilled off under reduced pressure. The oily product obtained was isolated by column chromatography (Wako Gel C-200, trade name, eluted with toluene:ethyl acetate=7:1) to give 0.4 g of the desired product as pale yellow liquid.

$n_D^{20.8}$ 1.5540.

EXAMPLE 16

Synthesis of dl-5-chloro-6-ethyl-4-[α-ethyl-4-(cyclopropylmethoxy)benzyl]aminopyrimidine (Compound No. 111)

To a solution of 1.1 g of dl-5-chloro-6-ethyl-4-(α-ethyl-4-hydroxybenzyl)aminopyrimidine dissolved in 30 ml of N,N-dimethylformamide was added 0.4 g of cyclopropylmethyl chloride, and the mixture was stirred at 90° to 100° C. for 8 hours. After completion of the reaction, the reaction mixture was charged into water and the separated oily product was extracted with ethyl acetate. The extract was washed with water, dried with anhydrous magnesium sulfate, and then the solvent was distilled off under reduced pressure. The oily product obtained was isolated by column chromatography (Wako Gel C-200, trade name, eluted with toluene:ethyl acetate=7:1) to give 0.5 g of the desired product as pale yellow liquid.

$n_D^{19.7}$ 1.5689.

EXAMPLE 17

Synthesis of dl-5-chloro-6-ethyl-4-[α-ethyl-4-(1,1,2,2-tetrafluoroethoxy)benzyl]aminopyrimidine (Compound No. 114)

Into a solution of 1.6 g of dl-5-chloro-6-ethyl-4-(α-ethyl-4-hydroxybenzyl)aminopyrimidine sodium salt dissolved in 30 ml of N,N-dimethylformamide was gradually bubbled about 2.2 g of tetrafluoroethylene at 80° C. under nitrogen atmosphere while stirring. After completion of the bubbling, the mixture was stirred for 2 hours, and the reaction mixture was charged into water and separated oily product was extracted with ethyl acetate. The extract was washed with water, dried over anhydrous sodium sulfate and ethyl acetate was distilled off under reduced pressure. The oily product obtained was isolated by column chromatography (Wako Gel C-200, trade name, eluted with toluene:ethyl acetate=7:1) to give 0.6 g of the desired product as pale yellow liquid.

$n_D^{15.0}$ 1.5213

EXAMPLE 18

Synthesis of dl-5-chloro-6-ethyl-4-(α-ethyl-4-acetonyloxybenzyl)aminopyrimidine (Compound No. 122)

To a solution of 3.0 g of dl-5-chloro-6-ethyl-4-(α-ethyl-4-hydroxybenzyl)aminopyrimidine dissolved in 30 ml of N,N-dimethylformamide were added 1.2 g of chloroacetone and 1.7 g of anhydrous potassium carbonate, and the mixture was stirred at 80° C. for 8 hours. After completion of the reaction, the reaction mixture was charged into water and the separated oily product was extracted with ethyl acetate. The extract was washed with water, dried with anhydrous sodium sulfate, and then ethyl acetate was distilled off under reduced pressure. The oily product obtained was isolated by column chromatography (Wako Gel C-200, trade name, eluted with toluene:ethyl acetate=7:1) to give 1.3 g of the desired product as pale yellow liquid.

$n_D^{15.6}$ 1.5654.

EXAMPLE 19

Synthesis of dl-5-chloro-6-ethyl-4-[α-ethyl-4-(2,2-difluoropropoxy)benzyl]aminopyrimidine (Compound No. 115)

To a solution of 1.0 g of dl-5-chloro-6-ethyl-4-(α-ethyl-4-acetonyloxybenzyl)aminopyrimidine obtained in Example 17 dissolved in 50 ml of dried benzene was added 0.5 g of diethylaminosulfur trifluoride, and the mixture was refluxed by heating for 5 hours while stirring. After completion of the reaction, the mixture was poured into ice-cold water and extracted with ethyl acetate. The extract was washed with water, dried over anhydrous sodium sulfate and the solvent was distilled off under reduced pressure. The oily product obtained was isolated by column chromatography (Wako Gel C-200, trade name, eluted with toluene:ethyl acetate=7:1) to give 0.6 g of the desired product as pale yellow oily liquid.

$n_D^{23.8}$ 1.5422.

EXAMPLE 20

Synthesis of dl-5-chloro-6-ethyl-4-[α-ethyl-4-(2,2-diethoxyethoxy)benzyl]aminopyrimidine (Compound No. 123)

To a solution of 5.0 g of dl-5-chloro-6-ethyl-4-(α-ethyl-4-hydroxybenzyl)aminopyrimidine sodium salt dissolved in 50 ml of N,N-dimethylformamide was added 4.8 g of bromoacetaldehyde diethylacetal, and the mixture was stirred at 80° C. for 8 hours. After completion of the reaction, the reaction mixture was charged into water and the separated oily product was extracted with ethyl acetate. The extract was washed with water, dried with anhydrous sodium sulfate, and then ethyl acetate was distilled off under reduced pressure. The oily product obtained was isolated by column chromatography (Wako Gel C-200, trade name, eluted with toluene:ethyl acetate=7:1) to give 2.3 g of the desired product as pale yellow liquid.

$n_D^{16.0}$ 1.5434.

Example 21

Synthesis of dl-5-chloro-6-ethyl-4-[α-ethyl-4-(1,3-dioxoran-2-ylmethoxy)benzyl]aminopyrimidine (Compound No. 124).

To a solution of 1.0 g of dl-5-chloro-6-ethyl-4-[α-ethyl-4-(2,2-diethoxyethoxy)benzyl]aminopyrimidine obtained in Example 19 dissolved in 60 ml of benzene were added 0.5 g of ethylene glycol and a catalytic amount of p-toluenesulfonic acid, and the mixture was refluxed by heating for 24 hours while stirring. After completion of the reaction, the reaction mixture was poured into ice-cold water and extracted with ethyl acetate. The extract was washed with water, dried with anhydrous sodium sulfate, and then the solvent was distilled off under reduced pressure. The residue was isolated by column chromatography (Wako Gel C-200, trade name, eluted with toluene:ethyl acetate=7:1 ) to give 0.2 g of the desired product as pale yellow powder.

melting point: 61° to 63° C.

EXAMPLE 22

Synthesis of dl-5-chloro-6-ethyl-4-[α-ethyl-4-(2-methoxyiminoethoxy)benzyl]aminopyrimidine (Compound No. 127)

To a solution of 1.0 g of dl-5-chloro-6-ethyl-4-[α-ethyl-4-(2,2-diethoxyethoxy)benzyl]aminopyrimidine obtained in Example 19 dissolved in 40 ml of ethanol was added 0.4 g of methoxyamine hydrochloride. Then, after addition of a catalytic amount of a 6N hydrochloric acid, the mixture was stirred at 60° C. for 2 hours. After completion of the reaction, the solvent was distilled off under reduced pressure and extracted with ethyl acetate. Then, the extract was washed with water, dried over anhydrous sodium sulfate and the solvent was distilled off under reduced pressure. The oily product obtained was isolated by column chromatography (Wako Gel C-200, trade name, eluted with toluene:ethyl acetate=7:1) to give 0.4 g of the desired product as pale yellow liquid.

$n_D^{19.4}$ 1.5678

EXAMPLE 23

Synthesis of dl-5-chloro-6-ethyl-4-[α-ethyl-4-(2-ethoxyethoxy)benzyl]aminopyrimidine (Compound No. 135)

To a solution of 1.2 g of dl-5-chloro-6-ethyl-4-(α-isopropyl-4-hydroxybenzyl)aminopyrimidine. sodium salt dissolved in 30 ml of N,N-dimethylformamide was added 0.6 g of bromoethyl ether, and the mixture was stirred at 80° C. for 8 hours. After completion of the reaction, the reaction mixture was poured into water and the separated oily product was extracted with ethyl acetate. The extract was washed with water, dried with anhydrous sodium sulfate, and then ethyl acetate was distilled off under reduced pressure. The oily product obtained was isolated by column chromatography (Wako Gel C-200, trade name, eluted with toluene:ethyl acetate 32 7:1) to give 0.6 g of the desired product as pale yellow liquid $n_D^{25.3}$ 1.5439.

EXAMPLE 24

The procedures were carried out in the same manner as in Examples 14 to 23 to give compounds indicated as Compounds Nos. 101, 104 to 110, 112, 113, 116 to 122, 125, 126, 128 to 134 and 136 to 143 shown in Table 2.

TABLE 2

| No. | Structural formula | Physical property |
|---|---|---|
| 101 | | $n_D^{17.2}$ 1.5492 |
| 102 | | $n_D^{17.2}$ 1.5444 |
| 103 | | $n_D^{20.8}$ 1.5540 |
| 104 | | $n_D^{16.5}$ 1.5356 |

TABLE 2-continued

| No. | Structural formula | Physical property |
|---|---|---|
| 105 | | $n_D^{24.6}$ 1.5627 |
| 106 | | $n_D^{20.7}$ 1.5580 |
| 107 | | $n_D^{12.5}$ 1.5544 |
| 108 | | $n_D^{13.6}$ 1.5620 |
| 109 | | $n_D^{17.0}$ 1.5754 |
| 110 | | $n_D^{16.8}$ 1.5870 |

TABLE 2-continued

| No. | Structural formula | Physical property |
|---|---|---|
| 111 | (pyrimidine-Cl-Et)-NH-CH(Et)-C6H4-OCH2-cyclopropyl | $n_D^{19.7}$ 1.5689 |
| 112 | (pyrimidine-Cl-Et)-NH-CH(Et)-C6H4-OCH2CH2F | $n_D^{19.5}$ 1.5611 |
| 113 | (pyrimidine-Cl-Et)-NH-CH(Et)-C6H4-OCH2CF2 | $n_D^{19.5}$ 1.5476 |
| 114 | (pyrimidine-Cl-Et)-NH-CH(Et)-C6H4-OCF2CHF2 | $n_D^{15.0}$ 1.5213 |
| 115 | (pyrimidine-Cl-Et)-NH-CH(Et)-C6H4-OCH2CF2CH3 | $n_D^{23.8}$ 1.5422 |
| 116 | (pyrimidine-Cl-Et)-NH-CH(Et)-C6H4-O-CH2CH2-O-Et | $n_D^{16.0}$ 1.5574 |
| 117 | (pyrimidine-Cl-Et)-NH-CH(Et)-C6H4-O-CH2CH2-O-CH2CH2-O-butyl | $n_D^{21.1}$ 1.5362 |

TABLE 2-continued

| No. | Structural formula | Physical property |
|---|---|---|
| 118 | (structure) | $n_D^{20.7}$ 1.5716 |
| 119 | (structure) | $n_D^{17.2}$ 1.5689 |
| 120 | (structure) | $n_D^{12.8}$ 1.5772 |
| 121 | (structure) | $n_D^{26.5}$ 1.5926 |
| 122 | (structure) | $n_D^{15.6}$ 1.5654 |
| 123 | (structure) | $n_D^{16.0}$ 1.5434 |

TABLE 2-continued

| No. | Structural formula | Physical property |
|---|---|---|
| 124 | | m.p. 61–63° C. |
| 125 | | $n_D^{17.0}$ 1.5806 |
| 126 | | $n_D^{15.5}$ 1.5464 |
| 127 | | $n_D^{19.4}$ 1.5678 |
| 128 | | $n_D^{23.4}$ 1.5599 |
| 129 | | $n_D^{23.0}$ 1.5810 |

TABLE 2-continued

| No. | Structural formula | Physical property |
|-----|---|---|
| 130 | | $n_D^{19.2}$ 1.5490 |
| 131 | | $n_D^{17.7}$ 1.5489 |
| 132 | | $n_D^{23.6}$ 1.5679 |
| 133 | | $n_D^{18.2}$ 1.5844 |
| 134 | | $n_D^{25.5}$ 1.5545 |
| 135 | | $n_D^{25.3}$ 1.5439 |
| 136 | | $n_D^{25.4}$ 1.5579 |

TABLE 2-continued

| No. | Structural formula | Physical property |
|---|---|---|
| 137 | (pyrimidine with Cl, Et)-NH-CH(Et)-C6H4-O-CH2CH2-O-C2H5 (meta) | $n_D^{24.2}$ 1.5495 |
| 138 | (pyrimidine with Cl, Et)-NH-CH(Et)-C6H4-OCH2CH2Br (para) | $n_D^{16.1}$ 1.5720 |
| 139 | (pyrimidine with Cl, Et)-NH-CH(Et)-C6H4-OC2H5 (para) | $n_D^{17.4}$ 1.5642 |
| 140 | (pyrimidine with Cl, CH3)-NH-CH(Et)-C6H4-O-CH2-cyclopropyl (para) | $n_D^{13.0}$ 1.5766 |
| 141 | (pyrimidine with Cl, CH3)-NH-CH(Et)-C6H4-O-CH2CH2-O-C2H5 (para) | $n_D^{14.6}$ 1.5665 |
| 142 | (pyrimidine with Cl, CH3)-NH-CH(Et)-C6H4-O-CH2-cyclopropyl (para) | $n_D^{20.6}$ 1.5726 |
| 143 | (pyrimidine with Cl, CH3)-NH-CH(Et)-C6H4-O-CH2CH2-O-CH3 (para) | $n_D^{19.8}$ 1.5602 |

TABLE 2-continued

| No. | Structural formula | Physical property |
|---|---|---|
| 144 | (structure: pyrimidine with NH linked to CH(cyclopropyl) attached to phenyl-O-CH2-cyclopropyl; pyrimidine bears Cl and ethyl substituents) | — |

EXAMPLE 25

Five (5) parts by weight of the compound of the Compound No. 1, 35 parts by weight of bentonite, 57 parts by weight of talc, 1 part by weight of Neopelex Powder (trade name, produced by Kao-Atlas Co.) and 2 parts by weight of sodium lignosulfate were homogeneously mixed, then kneaded with addition of a small amount of water, followed by granulation and drying to obtain granules.

EXAMPLE 26

Five (5) parts by weight of the compound of the Compound No. 69, 35 parts by weight of bentonite, 57 parts by weight of talc, 1 part by weight of Neopelex powder (trade name, produced by Kao-Atlas Co.) and 2 parts by weight of sodium lignosulfate were homogeneously mixed, then kneaded with addition of a small amount of water, followed by granulation and drying to obtain granules.

EXAMPLE 27

Fifty (50) parts by weight of the compound of the Compound No. 22, 48 parts by weight of kaolin and 2 parts by weight of Neopelex Powder (trade name, produced by Kao-Atlas Co.) were homogeneously mixed, followed by pulverization, to obtain wettable powder.

EXAMPLE 28

Fifty (50) parts by weight of the compound of the Compound No. 72, 48 parts by weight of kaolin and 2 parts by weight of Neopelex powder (trade name, produced by Kao-Atlas Co.) were homogeneously mixed, followed by pulverization, to obtain wettable powder.

EXAMPLE 29

To 20 parts by weight of the compound of the Compound No. 38 and 70 parts by weight of xylene were added 10 parts by weight of Toxanon (trade name, produced by Sanyo Kasei Kogyo, Co.), and homogeneously mixed and dissolved to obtain an emulsion.

EXAMPLE 30

To 20 parts by weight of the compound of the Compound No. 81 and 70 parts by weight of xylene were added 10 parts by weight of Toxanon (trade name, produced by Sanyo Kasei Kogyo, Co.), and homogeneously mixed and dissolved to obtain an emulsion.

EXAMPLE 31

Five (5) parts by weight of the compound of the Compound No. 12, 50 parts by weight of talc and 45 parts by weight of kaolin were homogeneously mixed to obtain powder.

EXAMPLE 32

Five (5) parts by weight of the compound of the Compound No. 83, 50 parts by weight of talc and 45 parts by weight of kaolin were homogeneously mixed to obtain powder.

EXAMPLE 33

Five (5) parts by weight of the compound of the Compound No. 102, 35 parts by weight of bentonite, 57 parts by weight of talc, 1 part by weight of Neopelex Powder (trade name, produced by Kao-Atlas Co.) and 2 parts by weight of sodium lignosulfate were homogeneously mixed, then kneaded with addition of a small amount of water, followed by granulation and drying to obtain granules.

EXAMPLE 34

Fifty (50) parts by weight of the compound of the Compound No. 111, 48 parts by weight of kaolin and 2 parts by weight of Neopelex Powder (trade name, produced by Kao-Atlas Co.) were homogeneously mixed, followed by pulverization, to obtain wettable powder.

EXAMPLE 35

To 20 parts by weight of the compound of the Compound No. 114 and 70 parts by weight of xylene were added 10 parts by weight of Toxanon (trade name, produced by Sanyo Kasei Kogyo, Co.), and homogeneously mixed and dissolved to obtain an emulsion.

EXAMPLE 36

Five (5) parts by weight of the compound of the Compound No. 115, 50 parts by weight of talc and 45 parts by weight of kaolin were homogeneously mixed to obtain powder.

EXAMPLE 37

Activity Test Against Tobacco Cutworm

The compounds shown in Tables 1 and 2 were formed into preparations similarly as in Examples 25, 26 and 33, diluted with water containing a surfactant (0.03 %) to 300 ppm. On the other hand, in plastic cups of 10 cm in diameter, leaves of soybean were laid, and 10 second in star larva of tabacco cutworm were provided for test on the leaves. The medicinal solution was sprayed each in 5 ml in a spraying tower. Then, the worm was left to stand in a thermostat chamber at 25° C., and the numbers of alive and dead insects were examined to determine the insecticide ratio. The results are shown in Table 3.

In Table 3, those with insecticide ratio of 100% are shown as 5, and those with insecticide ratio of 99 to 80% as 4.

As control, a compound represented by the following formula (hereinafter called as "Compound A") was used.

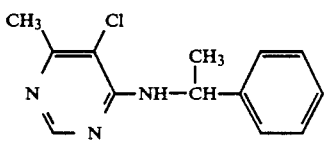

TABLE 3

| Compound No. | Effect |
| --- | --- |
| 1 | 4 |
| 3 | 5 |
| 9 | 4 |
| 11 | 4 |
| 13 | 4 |
| 14 | 4 |
| 17 | 5 |
| 18 | 5 |
| 19 | 5 |
| 20 | 5 |
| 22 | 5 |
| 24 | 5 |
| 25 | 5 |
| 32 | 5 |
| 33 | 4 |
| 34 | 5 |
| 35 | 4 |
| 36 | 5 |
| 37 | 5 |
| 38 | 5 |
| 39 | 5 |
| 40 | 4 |
| 41 | 5 |
| 43 | 4 |
| 45 | 4 |
| 46 | 5 |
| 47 | 5 |
| 48 | 5 |
| 49 | 5 |
| 50 | 5 |
| 51 | 4 |
| 53 | 4 |
| 54 | 4 |
| 60 | 4 |
| 61 | 5 |
| 62 | 5 |
| 63 | 5 |
| 65 | 5 |
| 68 | 5 |
| 69 | 5 |
| 72 | 5 |
| 76 | 5 |
| 79 | 5 |
| 80 | 4 |
| 82 | 5 |
| 83 | 5 |
| 87 | 5 |
| 94 | 5 |
| 103 | 5 |
| 109 | 5 |
| 111 | 5 |
| 112 | 5 |
| 114 | 5 |
| 115 | 5 |
| 120 | 5 |
| Compound A | No Effect |

EXAMPLE 36

Activity Test Against Diamondback Moth (Organic Phosphorus Agent Resistance)

In plastic cups of 10 cm in diameter, cabbage leave strip (5 cm×5 cm) were placed, while the medicinal solutions prepared by forming the compounds shown in Tables 1 and 2 into preparations similarly as in Examples 25, 26 and 33 and diluting with water containing a surfactant (0.03%) to 300 ppm were sprayed each in 5 ml in a spraying tower. After drying on air, 10 third-instar larva of diamondback moth were provided for test, left to stand in a thermostat chamber at 25° C. After 2 days, the numbers of alive and dead insects were examined to determine the insecticide ratio. The results are shown in Table 4.

In Table 4, those with insecticide ratio of 100% are shown as 5, and those with insecticide ratio of 99 to 80% as 4.

TABLE 4

| Compound No. | Effect |
| --- | --- |
| 1 | 5 |
| 3 | 5 |
| 11 | 4 |
| 13 | 5 |
| 14 | 4 |
| 17 | 5 |
| 18 | 5 |
| 19 | 5 |
| 20 | 5 |
| 22 | 5 |
| 24 | 5 |
| 25 | 5 |
| 32 | 5 |
| 33 | 4 |
| 34 | 5 |
| 35 | 5 |
| 36 | 5 |
| 37 | 5 |
| 38 | 5 |
| 39 | 5 |
| 40 | 5 |
| 41 | 5 |
| 43 | 5 |
| 44 | 5 |
| 45 | 5 |
| 46 | 5 |
| 47 | 5 |
| 48 | 5 |
| 49 | 5 |
| 50 | 5 |
| 51 | 5 |
| 53 | 4 |
| 54 | 5 |
| 60 | 5 |
| 61 | 5 |
| 62 | 5 |
| 63 | 5 |
| 65 | 5 |
| 68 | 5 |
| 69 | 5 |
| 71 | 5 |
| 72 | 5 |
| 74 | 4 |
| 75 | 5 |
| 76 | 5 |
| 78 | 4 |
| 79 | 4 |
| 80 | 5 |
| 82 | 5 |
| 83 | 5 |
| 84 | 5 |
| 85 | 4 |
| 86 | 4 |
| 87 | 4 |
| 88 | 4 |
| 89 | 4 |
| 92 | 5 |
| 93 | 4 |
| 94 | 5 |
| 101 | 5 |
| 102 | 4 |
| 103 | 5 |
| 104 | 4 |
| 105 | 5 |
| 111 | 5 |

TABLE 4-continued

| Compound No. | Effect |
| --- | --- |
| 112 | 5 |
| 113 | 5 |
| 114 | 5 |
| 115 | 5 |
| 116 | 4 |
| 117 | 5 |
| 120 | 4 |
| 121 | 4 |
| 122 | 4 |
| 124 | 5 |
| 127 | 5 |
| 128 | 5 |
| 131 | 5 |
| 132 | 5 |
| 133 | 5 |
| 139 | 5 |
| 142 | 5 |
| 143 | 4 |
| Compound A | No Effect |

EXAMPLE 37

Activity Test Against Brown Planthopper

In the medicinal solutions prepared by forming the compounds shown in Tables 1 and 2 into preparations similarly as in Examples 25, 26 and 33 and diluting with water containing a surfactant (0.03%) to 300 ppm, rice seedlings were dipped for 30 seconds and after drying on air inserted into a glass cylinder. Ten third-instar larva of brown planthopper were freed, and left to stand in a thermostat chamber at 25° C. with attachment of a porous stopper. After 2 days, the numbers of alive and dead insects were examined to determine the insecticide ratio. The results are shown in Table 5.

In Table 5, those with insecticide ratio of 100% are shown as 5, and those with insecticide ratio of 99 to 80% as 4.

TABLE 5

| Compound No. | Effect |
| --- | --- |
| 1 | 5 |
| 3 | 5 |
| 11 | 4 |
| 13 | 4 |
| 14 | 5 |
| 17 | 5 |
| 18 | 5 |
| 19 | 5 |
| 20 | 5 |
| 22 | 5 |
| 24 | 5 |
| 25 | 5 |
| 32 | 5 |
| 33 | 4 |
| 34 | 5 |
| 35 | 5 |
| 36 | 5 |
| 37 | 5 |
| 38 | 5 |
| 39 | 5 |
| 40 | 5 |
| 41 | 5 |
| 43 | 5 |
| 44 | 5 |
| 45 | 5 |
| 46 | 4 |
| 47 | 5 |
| 48 | 5 |
| 49 | 5 |
| 50 | 5 |
| 51 | 5 |
| 53 | 4 |
| 54 | 4 |
| 57 | 4 |
| 60 | 4 |
| 61 | 5 |
| 62 | 5 |
| 63 | 5 |
| 65 | 5 |
| 66 | 5 |
| 68 | 5 |
| 69 | 5 |
| 71 | 5 |
| 72 | 5 |
| 73 | 4 |
| 74 | 4 |
| 75 | 5 |
| 76 | 5 |
| 78 | 5 |
| 80 | 5 |
| 82 | 5 |
| 83 | 5 |
| 84 | 4 |
| 87 | 5 |
| 88 | 5 |
| 89 | 4 |
| 91 | 4 |
| 93 | 5 |
| 94 | 5 |
| 101 | 5 |
| 102 | 4 |
| 103 | 5 |
| 104 | 5 |
| 108 | 5 |
| 111 | 5 |
| 112 | 5 |
| 113 | 5 |
| 114 | 5 |
| 115 | 5 |
| 116 | 5 |
| 117 | 5 |
| 120 | 5 |
| 121 | 5 |
| 122 | 4 |
| 123 | 4 |
| 124 | 4 |
| 128 | 5 |
| 130 | 5 |
| 131 | 5 |
| 132 | 5 |
| 133 | 5 |
| 139 | 4 |
| 142 | 5 |
| 143 | 5 |
| Compound A | No Effect |

EXAMPLE 38

Activity Test Against Green Rice Leafhopper (organic phosphorus agent resistance)

In the medicinal solutions prepared by forming the compounds shown in Tables 1 and 2 into preparations similarly as in Examples 25, 26 and 33 and diluting with water containing a surfactant (0.03%) to 300 ppm, rice seedlings were dipped for 30 seconds and after drying on air inserted into a glass cylinder. Ten third-instar larva of green rice leafhopper were freed, and left to stand in a thermostat chamber at 25° C. with attachment of a porous stopper. After 2 days, the numbers of alive and dead insects were examined to determine the insecticide ratio. The results are shown in Table 6.

In Table 6, those with insecticide ratio of 100% are shown as 5, and those with insecticide ratio of 99 to 80% as 4.

TABLE 6

| Compound No | Effect |
| --- | --- |
| 1 | 5 |
| 3 | 5 |
| 11 | 4 |
| 13 | 4 |
| 14 | 4 |
| 17 | 5 |
| 18 | 5 |
| 19 | 5 |
| 20 | 5 |
| 22 | 5 |
| 24 | 5 |
| 25 | 5 |
| 32 | 5 |
| 33 | 5 |
| 34 | 4 |
| 35 | 4 |
| 36 | 5 |
| 37 | 5 |
| 38 | 5 |
| 39 | 5 |
| 40 | 4 |
| 41 | 5 |
| 43 | 5 |
| 44 | 5 |
| 45 | 5 |
| 46 | 4 |
| 47 | 5 |
| 48 | 5 |
| 49 | 5 |
| 50 | 5 |
| 51 | 5 |
| 53 | 5 |
| 54 | 4 |
| 57 | 4 |
| 60 | 4 |
| 61 | 4 |
| 62 | 5 |
| 63 | 5 |
| 65 | 5 |
| 66 | 4 |
| 68 | 5 |
| 69 | 5 |
| 71 | 4 |
| 72 | 5 |
| 73 | 5 |
| 74 | 4 |
| 75 | 5 |
| 76 | 5 |
| 77 | 4 |
| 78 | 5 |
| 80 | 5 |
| 82 | 5 |
| 83 | 5 |
| 84 | 5 |
| 87 | 5 |
| 88 | 5 |
| 89 | 5 |
| 93 | 5 |
| 94 | 5 |
| 101 | 5 |
| 102 | 5 |
| 103 | 5 |
| 105 | 5 |
| 108 | 5 |
| 109 | 5 |
| 110 | 5 |
| 111 | 5 |
| 112 | 5 |
| 113 | 5 |
| 114 | 5 |
| 115 | 5 |
| 116 | 5 |
| 120 | 4 |
| 121 | 4 |
| 122 | 5 |
| 123 | 5 |
| 127 | 4 |
| 128 | 5 |
| 131 | 5 |
| 132 | 5 |
| 133 | 5 |
| 142 | 5 |
| 143 | 5 |
| Compound A | No Effect |

EXAMPLE 39

Activity Test Against Adult Female Two-spotted Spider Mite (Organic Phosphorus Agent Resistance)

On a filter paper soaked with water, kidney bean leave strips of 20 mm in diameter were placed and 10 adult female two-spotted spider mites were inoculated. The leave strips were dipped for 15 seconds in medicinal solutions prepared by forming the compounds shown in Tables 1 and 2 into preparations similarly as in Examples 25, 26 and 33 and diluting with water containing a surfactant (0.03%) to 300 ppm. After drying on air, the leave strip were left to stand in a thermostat chamber at 30° C. After 3 days, the numbers of alive and dead insects were examined to determine the acaricide ratio. The results are shown in Table 7.

In Table 7, those with acaricide ratio of 100% are shown as 5, and those with acaricide ratio of 99 to 80% as 4.

TABLE 7

| Compound No. | Effect |
| --- | --- |
| 1 | 4 |
| 3 | 5 |
| 17 | 5 |
| 18 | 5 |
| 19 | 5 |
| 20 | 4 |
| 22 | 5 |
| 24 | 5 |
| 25 | 5 |
| 32 | 5 |
| 33 | 5 |
| 34 | 5 |
| 35 | 4 |
| 37 | 4 |
| 38 | 4 |
| 39 | 5 |
| 41 | 5 |
| 42 | 5 |
| 47 | 5 |
| 48 | 5 |
| 49 | 5 |
| 50 | 5 |
| 57 | 5 |
| 60 | 5 |
| 61 | 5 |
| 62 | 5 |
| 63 | 5 |
| 65 | 5 |
| 68 | 5 |
| 69 | 5 |
| 71 | 5 |
| 72 | 5 |
| 75 | 4 |
| 79 | 4 |
| 80 | 5 |
| 82 | 5 |
| 83 | 4 |
| 87 | 4 |
| 90 | 4 |
| 91 | 5 |
| 94 | 4 |
| 101 | 5 |
| 102 | 5 |
| 103 | 5 |
| 105 | 5 |

TABLE 7-continued

| Compound No. | Effect |
|---|---|
| 106 | 5 |
| 108 | 5 |
| 109 | 5 |
| 110 | 5 |
| 111 | 5 |
| 112 | 5 |
| 113 | 5 |
| 114 | 5 |
| 115 | 5 |
| 116 | 5 |
| 117 | 5 |
| 119 | 4 |
| 120 | 5 |
| 122 | 4 |
| 123 | 5 |
| 124 | 5 |
| 125 | 5 |
| 127 | 5 |
| 128 | 5 |
| 130 | 5 |
| 131 | 5 |
| 132 | 5 |
| 138 | 5 |
| 139 | 5 |
| 140 | 4 |
| 142 | 5 |
| 143 | 5 |
| Compound A | No effect |

EXAMPLE 40

Activity Test Against Two-spotted Spider Mite Egg (Organic Phosphorus Agent Resistance)

On a filter paper soaked with water, kidney bean leave strips of 20 mm in diameter were placed and 5 adult female two-spotted spider mites were inoculated and permitted to lay eggs for one day. Next, the adult female mites were removed, ad each kidney leave strip on which eggs were laid was dipped for 15 seconds into medicinal solutions prepared by forming the compounds shown in Tables 1 and 2 into preparations similarly as in Examples 25, 26 and 33 and diluting with water containing a surfactant (0.03%) to 300 ppm. After drying on air, the leave strip were left to stand in a thermostat chamber at 25° C. On the day 8 after the treatment, the number of non-hatched eggs was examined to determine the egg killing ratio. The results are shown in Table 8.

In Table 8, those with egg killing ratio of 100% are shown as 5, and those with egg killing ratio of 99 to 80% as 4.

TABLE 8

| Compound No. | Effect |
|---|---|
| 1 | 5 |
| 2 | 5 |
| 3 | 5 |
| 11 | 4 |
| 17 | 5 |
| 18 | 5 |
| 19 | 5 |
| 20 | 5 |
| 22 | 5 |
| 24 | 5 |
| 25 | 5 |
| 31 | 5 |
| 32 | 5 |
| 33 | 5 |
| 34 | 5 |
| 36 | 5 |
| 37 | 5 |
| 38 | 5 |
| 39 | 5 |
| 40 | 4 |
| 41 | 5 |
| 42 | 5 |
| 47 | 5 |
| 48 | 5 |
| 49 | 5 |
| 50 | 5 |
| 51 | 5 |
| 53 | 5 |
| 54 | 5 |
| 57 | 5 |
| 60 | 5 |
| 61 | 5 |
| 62 | 5 |
| 63 | 5 |
| 65 | 5 |
| 68 | 5 |
| 69 | 5 |
| 71 | 5 |
| 72 | 5 |
| 73 | 5 |
| 74 | 5 |
| 75 | 5 |
| 79 | 5 |
| 80 | 5 |
| 82 | 5 |
| 83 | 5 |
| 87 | 5 |
| 88 | 4 |
| 89 | 5 |
| 92 | 5 |
| 93 | 5 |
| 94 | 5 |
| 101 | 5 |
| 102 | 5 |
| 103 | 5 |
| 104 | 5 |
| 105 | 5 |
| 106 | 5 |
| 108 | 5 |
| 109 | 5 |
| 110 | 5 |
| 111 | 5 |
| 112 | 5 |
| 113 | 5 |
| 114 | 5 |
| 115 | 5 |
| 116 | 5 |
| 117 | 5 |
| 120 | 5 |
| 123 | 5 |
| 124 | 5 |
| 125 | 5 |
| 127 | 5 |
| 128 | 5 |
| 129 | 5 |
| 130 | 5 |
| 131 | 5 |
| 132 | 5 |
| 138 | 5 |
| 139 | 5 |
| 140 | 5 |
| 141 | 5 |
| 142 | 5 |
| 143 | 5 |
| Compound A | No effect |

EXAMPLE 41

Activity Test Against Adult Female Citrus Red Mite (Organic Phosphorus Agent Resistance)

On a filter paper soaked with water, mulberry leave strips of 20 mm in diameter were placed and 10 adult female citrus red mites were introduced. On the other hand, the medicinal solutions prepared by forming the compounds shown in Tables 1 and 2 into preparations similarly as in Examples 25, 26 and 33 and diluting with water containing a surfactant (0.03%) to 300 ppm were sprayed each in 5 ml in a spraying tower. After the treatment, each strip was left to stand in a thermostat chamber at 25° C., and after 3 days, the numbers of alive and dead mites were examined to determine the acaricide ratio. The results are shown in Table 9.

In Table 9, those with acaricide ratio of 100% are shown as 5, and those with acaricide ratio of 99 to 80% as 4.

TABLE 9

| Compound No. | Effect |
| --- | --- |
| 1 | 5 |
| 2 | 4 |
| 3 | 5 |
| 11 | 5 |
| 12 | 4 |
| 13 | 4 |
| 17 | 5 |
| 18 | 5 |
| 19 | 5 |
| 20 | 5 |
| 22 | 5 |
| 24 | 5 |
| 25 | 5 |
| 30 | 5 |
| 32 | 5 |
| 33 | 5 |
| 34 | 5 |
| 35 | 5 |
| 36 | 4 |
| 37 | 5 |
| 38 | 5 |
| 39 | 5 |
| 40 | 5 |
| 41 | 5 |
| 47 | 5 |
| 48 | 5 |
| 49 | 5 |
| 50 | 5 |
| 53 | 5 |
| 57 | 5 |
| 60 | 4 |
| 61 | 5 |
| 62 | 5 |
| 63 | 5 |
| 65 | 5 |
| 68 | 5 |
| 69 | 5 |
| 71 | 5 |
| 72 | 5 |
| 75 | 5 |
| 79 | 5 |
| 80 | 5 |
| 82 | 5 |
| 83 | 4 |
| 87 | 5 |
| 89 | 5 |
| 94 | 4 |
| 101 | 5 |
| 102 | 5 |
| 103 | 5 |
| 105 | 5 |
| 106 | 5 |
| 108 | 5 |
| 109 | 5 |
| 110 | 5 |
| 111 | 5 |
| 112 | 4 |
| 113 | 5 |
| 114 | 5 |
| 116 | 5 |
| 117 | 5 |
| 120 | 5 |
| 123 | 5 |
| 124 | 5 |
| 125 | 5 |
| 127 | 5 |
| 128 | 5 |
| 130 | 5 |
| 131 | 5 |
| 132 | 5 |
| 139 | 5 |
| 142 | 5 |
| 143 | 5 |
| Compound A | No effect |

EXAMPLE 42

Activity Test Against Citrus Red Mite Egg (Organic Phosphorus Agent Resistance)

On a filter paper soaked with water, mulberry leave strips of 20 mm in diameter were placed and 5 adult female citrus red mites were inoculated and permitted to lay eggs for one day. On the other hand, the medicinal solutions prepared by forming the compounds shown in Tables 1 and 2 into preparations similarly as in Examples 25, 26 and 33 and diluting with water containing a surfactant (0.03%) to 300 ppm were sprayed each in 5 ml in a spraying tower. After the treatment, each strip was left to stand in a thermostat chamber at 25° C., and after 10 days, the numbers of non-hatched eggs were examined to determine the egg killing ratio. The results are shown in Table 10.

In Table 10, those with egg killing ratio of 100% are shown as 5, and those with egg killing ratio of 99 to 80% as 4.

TABLE 10

| Compound No. | Effect |
| --- | --- |
| 1 | 5 |
| 3 | 5 |
| 11 | 5 |
| 17 | 5 |
| 18 | 5 |
| 19 | 5 |
| 20 | 5 |
| 22 | 5 |
| 24 | 5 |
| 25 | 5 |
| 30 | 4 |
| 32 | 5 |
| 33 | 4 |
| 34 | 5 |
| 35 | 5 |
| 36 | 4 |
| 37 | 5 |
| 38 | 5 |
| 39 | 5 |
| 41 | 5 |
| 47 | 5 |
| 48 | 5 |
| 49 | 5 |
| 50 | 5 |
| 53 | 5 |
| 57 | 5 |
| 60 | 4 |
| 61 | 4 |
| 62 | 5 |
| 63 | 5 |
| 65 | 5 |
| 68 | 5 |
| 69 | 5 |
| 71 | 5 |
| 72 | 5 |
| 75 | 5 |
| 79 | 5 |
| 80 | 5 |
| 82 | 5 |
| 83 | 5 |

TABLE 10-continued

| Compound No. | Effect |
|---|---|
| 87 | 5 |
| 88 | 4 |
| 89 | 5 |
| 94 | 5 |
| 101 | 5 |
| 102 | 5 |
| 103 | 5 |
| 105 | 5 |
| 106 | 5 |
| 108 | 5 |
| 109 | 5 |
| 110 | 5 |
| 111 | 5 |
| 112 | 5 |
| 113 | 5 |
| 114 | 5 |
| 115 | 5 |
| 116 | 5 |
| 117 | 5 |
| 120 | 5 |
| 122 | 5 |
| 123 | 5 |
| 124 | 5 |
| 125 | 5 |
| 127 | 5 |
| 128 | 5 |
| 130 | 5 |
| 131 | 5 |
| 132 | 5 |
| 138 | 5 |
| 139 | 5 |
| 142 | 5 |
| 143 | 5 |
| Compound A | No effect |

EXAMPLE 43

Control Effect Against Blast

In pots made of a plastic, soil medium was placed and rice seeds were planted. Cultivation was conducted in a hot house, and on the young seedlings with the main leave spread to 3.5 leave was sprayed sufficient amounts of the medicinal solutions prepared by forming the compounds shown in Tables 1 and 2 into preparations similarly as in Examples 25, 26 and 33 and diluting with water containing a surfactant (0.01%) to 200 ppm. After 48 hours after spraying, a suspension of spores of *Piricularia orizae* was inoculated by spraying, and after standing in a disease developing housing at a temperature of 25° C. and a humidity of 100% for 4 days, the number of lesion was measured. The effect of medicine was judged by comparison with the number of lesion in the non-treated district. Evaluation is shown at 6 ranks of 5 to 0, with no lesion being rated as 5, those with lesion area of 10% or less as compared with the non-treated district as 4, those with about 20% as 3, those with about 40% as 2, those with about 60 % as 1, and those wholly afflicted with disease as 0. The results are shown in Table 11.

TABLE 11

| Compound No. | Effect |
|---|---|
| 3 | 4 |
| 7 | 5 |
| 18 | 4 |
| 19 | 4 |
| 20 | 5 |
| 21 | 5 |
| 22 | 4 |
| 25 | 4 |
| 26 | 3 |
| 32 | 3 |

TABLE 11-continued

| Compound No. | Effect |
|---|---|
| 33 | 5 |
| 34 | 4 |
| 37 | 5 |
| 43 | 4 |
| 44 | 3 |
| 50 | 4 |
| 51 | 4 |
| 55 | 5 |
| 56 | 5 |
| 68 | 4 |
| 69 | 4 |
| 71 | 4 |
| 72 | 4 |
| 75 | 4 |
| 81 | 4 |
| 86 | 4 |
| 93 | 4 |
| 101 | 4 |
| 102 | 4 |
| 103 | 4 |
| 104 | 4 |
| 105 | 5 |
| 108 | 5 |
| 110 | 4 |
| 111 | 5 |
| 112 | 5 |
| 116 | 4 |
| 120 | 5 |
| 121 | 4 |
| 127 | 4 |
| 130 | 5 |
| 141 | 4 |
| Non-treated district | 0 |

EXAMPLE 44

Control Effect Against Downy Mildew

In pots made of a plastic, soil medium was placed and cucumber seeds were planted. Cultivation was conducted in a hot house, and on the young seedlings with spreading of the first leave was sprayed sufficient amounts of the medicinal solutions prepared similarly as described in Examples 25, 26 and 33 and diluting with water containing a surfactant (0.01%) to 200 ppm. After 48 hours after spraying, a suspension of spores of *Pseudoperonospora cubensis* was inoculated by spraying and left to stand in a chamber at a temperature of 25° C. and a humidity of 100% for 24 hours. The effect of medicine was judged by comparison with the number of lesion in the non-treated district by observation with eyes of the lesion area on the day 10 after inoculation. Evaluation is shown at 6 ranks of 5 to 0, with no lesion being rated as 5, those with lesion area of 10% or less as compared with the non-treated district as 4, those with about 20% as 3, those with about 40% as 2, those with about 60% as 1, and those wholly afflicted with disease as 0. The results are shown in Table 12.

TABLE 12

| Compound No. | Effect |
|---|---|
| 3 | 5 |
| 7 | 5 |
| 8 | 4 |
| 11 | 5 |
| 18 | 4 |
| 19 | 5 |
| 20 | 5 |
| 21 | 4 |
| 22 | 5 |
| 24 | 5 |

TABLE 12-continued

| Compound No. | Effect |
| --- | --- |
| 25 | 4 |
| 26 | 3 |
| 32 | 4 |
| 34 | 5 |
| 35 | 3 |
| 37 | 5 |
| 38 | 5 |
| 39 | 5 |
| 40 | 5 |
| 41 | 5 |
| 43 | 5 |
| 44 | 5 |
| 45 | 5 |
| 46 | 3 |
| 51 | 5 |
| 53 | 4 |
| 54 | 3 |
| 60 | 4 |
| 68 | 5 |
| 69 | 4 |
| 71 | 4 |
| 72 | 5 |
| 75 | 4 |
| 80 | 4 |
| 81 | 4 |
| 84 | 4 |
| 88 | 4 |
| 89 | 4 |
| 109 | 4 |
| 110 | 4 |
| 111 | 4 |
| 113 | 5 |
| 114 | 5 |
| 115 | 4 |
| 118 | 4 |
| 120 | 5 |
| 121 | 4 |
| 128 | 4 |
| 130 | 4 |
| 139 | 4 |
| Non-treated district | 0 |

EXAMPLE 45

Control Effect Against Powdery Mildew

In pots made of a plastic, soil medium was placed and barley seeds were planted. Cultivation was conducted in a hot house, and on the young seedlings with spreading of the second leave was sprayed sufficient amounts of the medicinal solutions prepared similarly as described in Examples 25, 26 and 33 and diluting with water containing a surfactant (0.01%) to 200 ppm. After 48 hours after spraying, a suspension of spores of *Erysphe graminis* was inoculated uniformly by spraying and left to stand in a chamber at a temperature of 20° C. and a humidity of 100% for 24 hours. On the day 7 after inoculation, the effect of medicine was judged by determining the number of lesion. Evaluation is shown at 6 ranks of 5 to 0, with no lesion being rated as 5, those with lesion area of 10 % or less as compared with the non-treated district as 4, those with about 20% as 3, those with about 40% as 2, those with about 60% as 1, and those wholly afflicted with disease as 0. The results are shown in Table 13.

TABLE 13

| Compound No. | Effect |
| --- | --- |
| 6 | 5 |
| 8 | 5 |
| 32 | 4 |

TABLE 13-continued

| Compound No. | Effect |
| --- | --- |
| 34 | 5 |
| 35 | 4 |
| 37 | 5 |
| 38 | 5 |
| 40 | 4 |
| 41 | 5 |
| 42 | 5 |
| 43 | 5 |
| 44 | 5 |
| 45 | 5 |
| 50 | 5 |
| 51 | 5 |
| 53 | 5 |
| 54 | 5 |
| 109 | 3 |
| 110 | 5 |
| 112 | 4 |
| 113 | 3 |
| 114 | 4 |
| 115 | 4 |
| 120 | 4 |
| 123 | 4 |
| 124 | 4 |
| 132 | 4 |
| 134 | 4 |
| 137 | 4 |
| 139 | 5 |
| Non-treated district | 0 |

According to the present invention, novel aralkyl amino-pyrimidine derivatives having excellent insecticide effect, acaricide effect and fungicide effect can be provided.

We claim:

1. An acaricidal composition comprising (i) an acaricidal carrier and (ii) as the active ingredient a compound represented by the formula:

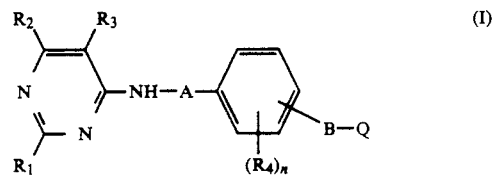

(I)

wherein $R_1$ represents a hydrogen atom or a lower alkyl group which is unsubstituted or substituted with a halogen atom; $R_2$ and $R_3$ each independently represent a halogen atom or a lower alkyl group which is unsubstituted or substituted with a halogen atom, a lower alkoxy group or a lower alkylthio group; $R_4$ represents a hydrogen atom, a halogen atom or a lower alkyl group; n represents an integer of 1 or 2; Q represents a phenyl group or a heterocyclic group selected from the group consisting of a furyl group, a thienyl group, a pyrrolyl group, an oxazolyl group, an isooxazolyl group, a thiazolyl group, an isothiazolyl group, an imidazolyl group, a pyrazolyl group, an oxadiazolyl group, a tetrazolyl group, a pyranyl group, a pyridyl group, a pyridazinyl group, a pyrimidinyl group, a pyrazinyl group, a symmetrical triazinyl group, a benzoxazolyl group, a benzoxozoyl group, a benzoimidazolyl group, a quinazolinyl group, a quinolyl group and a quinoxalinyl group each of which phenyl and heterocyclic group is unsubstituted or substituted with at least one selected from the group consisting of a halogen atom, a nitro group, a lower alkoxy group, a lower alkylthio group, a lower alkyl group which is unsubstituted or substituted with a halogen atom or a lower alkoxy group, a phenyl group which is unsubstituted or substituted with a lower alkoxy group and a phenoxy group which is unsubstituted or substituted with a halogen atom or an unsubstituted or halogen atom-substituted lower alkyl group; said heterocyclic group may be substituted with an oxo group; an alkyl group having 5 to 10 carbon atoms; an allyl group; a geranyl group; a farnesyl group; a lower alkyl group substituted with 1 to 4 halogen atoms; a cycloalkylmethyl group having 3 to 6 carbon atoms; an ethyl group substituted with a lower alkoxy group, a lower alkoxyalkyl group, a lower alkylthio group, a lower alkylsulfonyl group or a phenoxy group which may be substituted with one or two lower alkyl groups; a glycidyl group; an acetonyl group; a dioxoranyl group substituted with a phenoxymethyl group which may be substituted with a chlorine atom; a 2,2-diethoxyethyl group, a 1-ethoxycarbonylethyl group, a trimethylsilylmethyl group, a 1-pyridylethyl group, a lower alkyl group substituted with a benzylimino group which may be substituted with a lower alkoxyimino group or a lower alkyl group; A represents a lower alkylene group which is unsubstituted or substituted with one or two substituents selected from the group consisting of a cycloalkyl group having 3 to 5 carbon atoms, a lower alkynyl group, a lower alkyl group substituted with a halogen atom, a lower alkoxy group or a lower alkylthio group; and B represents a direct bond, an oxygen atom, a sulfur atom, a straight or branched lower alkylene group or a lower alkyleneoxy group; or an acid addition salt thereof.

2. The acaricidal composition of claim 1 wherein said compound of the formula (I) is selected from the group consisting of dl-5-chloro-6-ethyl-4-(alpha-ethyl-3-phenoxy-benzyl-)aminopyrimidine;
dl-5-chloro-6-ethyl-4-(α-isopropyl-4-phenoxy)benzyl]aminopyrimidine;
dl-5-chloro-6-ethyl-4-[α-ethyl-4-(4-fluorophenoxy)-benzyl]aminopyrimidine;
dl-5-chloro-6-ethyl-4-[α-ethyl-4-(3-pyridyloxy)benzyl]aminopyrimidine;
dl-5-chloro-6-ethyl-4-[α-ethyl-4-(5-nitropyridin-2-yloxy)benzyl]aminopyrimidine;
dl-5-chloro-6-ethyl-4-[α-ethyl-4-(5-chloro-6-ethylpyrimidin-4-yloxy) benzyl]aminopyrimidine;
dl-5-chloro-6-ethyl-4-[α-ethyl-4-(2-pyrimidyloxy)-benzyl]aminopyrimidine;
dl-5-chloro-6-ethyl-4-[α-ethyl-4-(isoamyloxy)benzyl-]aminopyrimidine;
dl-5-chloro-6-ethyl-4-[α-ethyl-4-(sec amyloxy)benzyl]aminopyrimidine;
dl-5-chloro-6-ethyl-4-[α-ethyl-4-(sec amyloxy)benzyl]aminopyrimidine;
dl-5-chloro-6-ethyl-4-[α-ethyl-4-(cyclopropylmethoxy)benzyl]aminopyrimidine;
dl-5-chloro-6-ethyl-4-[α-ethyl-4-(1,1,2,2-tetrafluoroethoxy)benzyl]aminopyrimidine;
dl-5-chloro-6-ethyl-4-[α-ethyl-4-(2,2-difluoropropoxy)-benzyl]aminopyrimidine;
dl-5-chloro-6-ethyl-4-(α-ethyl-4-acetonyloxybenzyl-)aminopyrimidine;
dl-5-chloro-6-ethyl-4-[α-ethyl-4-(2,2-diethoxyethoxy)-benzyl]aminopyrimidine;
dl-5-chloro-6-ethyl-4-[α-ethyl-4-(1,3-dioxoran-2-yl-methoxy)benzyl]aminopyrimidine;
dl-5-chloro-6-ethyl-4-[α-ethyl-4-(2-methexyiminoethoxy)benzyl]aminopyrimidine; and
dl-5-chloro-6-ethyl-4-[α-ethyl-4-(2-ethoxyethoxy)-benzyl]aminopyrimidine.

3. A fungicidal composition comprising (i) a fungicidal carrier and (ii) as the active ingredient a compound represented by the formula:

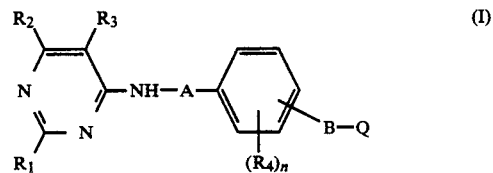

wherein $R_1$ represents a hydrogen atom or a lower alkyl group which is unsubstituted or substituted with a halogen atom; $R_2$ and $R_3$ each independently represent a halogen atom or a lower alkyl group which is unsubstituted or substituted with a halogen atom, a lower alkoxy group or a lower alkylthio group; $R_4$ represents a hydrogen atom, a halogen atom or a lower alkyl group; n represents an integer of 1 or 2; Q represents a phenyl group or a heterocyclic group selected from the group consisting of a furyl group, a thienyl group, a pyrrolyl group, an oxazolyl group, an isooxazolyl group, a thiazolyl group, an isothiazolyl group, an imidazolyl group, a pyrazolyl group, an oxadiazolyl group, a tetrazolyl group, a pyranyl group, a pyridyl group, a pyridazinyl group, a pyrimidinyl group, a pyrazinyl group, a symmetrical triazinyl group, a benzoxazolyl group, a benzoxozoyl group, a benzoimidazolyl group, a quiuazolinyl group, a quinolyl group and a quinoxalinyl group each of which phenyl and heterocyclic group is unsubstituted or substituted with at least one selected from the group consisting of a halogen atom, a nitro group, a lower alkoxy group, a lower alkylthio group, a lower alkyl group which is unsubstituted or substituted with a halogen atom or a lower alkoxy group, a phenyl group which is unsubstituted or substituted with a lower alkoxy group and a phenoxy group which is unsubstituted or substituted with a halogen atom or an unsubstituted or halogen atom-substituted lower alkyl group; said heterocyclic group may be substituted with an oxo group; an alkyl group having 5 to 10 carbon atoms; an allyl group; a geranyl group; a farnesyl group; a lower alkyl group substituted with 1 to 4 halogen atoms; a cycloalkylmethyl group having 3 to 6 carbon atoms; an ethyl group substituted with a lower alkoxy group, a lower alkoxyalkyl group, a lower alkylthio group, a lower alkylsulfonyl group or a phenoxy group which may be substituted with one or two lower alkyl groups; a glycidyl group; an acetonyl group; a dioxoranyl group substituted with a phenoxymethyl group which may be substituted with a chlorine atom; a 2,2-diethoxyethyl group, a 1-ethoxycarbonylethyl group, a trimethylsilylmethyl group, a 1-pyridylethyl group, a lower alkyl group substituted with a benzylimino group which may be substituted with a lower alkoxyimino group or a lower alkyl group; A represents a lower alkylene group which is unsubstituted or substituted with one or two substituents selected from the group consisting of a cycloalkyl group having 3 to 5 carbon atoms, a lower alkynyl group, a lower alkyl group substituted with a halogen atom, a lower alkoxy group or a lower alkylthio group; and B represents a direct bond, an oxygen atom, a sulfur atom, a straight or branched lower alkylene group or a lower alkyleneoxy group; or an acid addition salt thereof.

4. The fungicidal composition of claim 3 wherein said compound of the formula (I) is selected from the group consisting of dl-5-chloro-6-ethyl-4-(alpha-ethyl-3-phenoxy-benzyl)aminopyrimidine;
dl-5-chloro-6-ethyl-4-(α-isopropyl-4-phenoxy)benzyl]aminopyrimidine;
dl-5-chloro-6-ethyl-4-[α-ethyl-4-(4-fluorophenoxy)-benzyl]aminopyrimidine;
dl-5-chloro-6-ethyl-4-[α-ethyl-4-(3-pyridyloxy)benzyl]aminopyrimidine;
dl-5-chloro-6-ethyl-4-[α-ethyl-4-(5-nitropyridin-2-yloxy)benzyl)]aminopyrimidine;
dl-5-chloro-6-ethyl-4-[α-ethyl-4-(5-chloro-6-ethylpyrimidin-4-yloxy)benzyl]aminopyrimidine;
dl-5-chloro-6-ethyl-4-[α-ethyl-4-(2-pyrimidyloxy)-benzyl]aminopyrimidine;
dl-5-chloro-6-ethyl-4-[α-ethyl-4-(isoamyloxy)benzyl]aminopyrimidine;
dl-5-chloro-6-ethyl-4-[α-ethyl-4-(sec amyloxy)benzyl]aminopyrimidine;
dl-5-chloro-6-ethyl-4-[α-ethyl-4-(sec amyloxy)benzyl]aminopyrimidine;
dl-5-chloro-6-ethyl-4-[α-ethyl-4-(cyclopropylmethoxy)benzyl]aminopyrimidine;
dl-5-chloro-6-ethyl-4-[α-ethyl-4-(1,1,2,2-tetrafluoroethoxy)benzyl]aminopyrimidine;
dl-5-chloro-6-ethyl-4-[α-ethyl-4-(2,2-difluoropropoxy)-benzyl]aminopyrimidine;
dl-5-chloro-6-ethyl-4-(α-ethyl-4-acetonyloxybenzyl)aminopyrimidine;
dl-5-chloro-6-ethyl-4-[α-ethyl-4-(2,2-diethoxyethoxy)-benzyl]aminopyrimidine;
dl-5-chloro-6-ethyl-4-[α-ethyl-4-(1,3-dioxoran-2-ylmethoxy)benzyl]aminopyrimidine;
dl-5-chloro-6-ethyl-4-[α-ethyl-4-(2-methexyiminoethoxy)benzyl]aminopyrimidine; and
dl-5-chloro-6-ethyl-4-[α-ethyl-4-(2-ethoxyethoxy)-benzyl]aminopyrimidine.

* * * * *